US008248588B2

(12) United States Patent
Azimi et al.

(10) Patent No.: US 8,248,588 B2
(45) Date of Patent: *Aug. 21, 2012

(54) HANDHELD INFRARED AND RAMAN MEASUREMENT DEVICES AND METHODS

(75) Inventors: Masud Azimi, Belmont, MA (US);
Arran Bibby, Savannah, GA (US);
Christopher D. Brown, Albuquerque, NM (US); Peili Chen, Andover, MA (US); Kevin J. Knopp, Newburyport, MA (US); Daryoosh Vakhshoori, Cambridge, MA (US); Peidong Wang, Carlisle, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,753

(22) Filed: Apr. 15, 2011

(65) Prior Publication Data

US 2011/0309247 A1 Dec. 22, 2011

Related U.S. Application Data

(63) Continuation of application No. 12/691,047, filed on Jan. 21, 2010, now Pat. No. 7,928,391, which is a continuation of application No. 11/864,304, filed on Sep. 28, 2007, now Pat. No. 7,675,611.

(60) Provisional application No. 60/931,086, filed on May 21, 2007.

(51) Int. Cl.
*G01N 21/25* (2006.01)
(52) U.S. Cl. ............... 356/73; 356/445; 356/301
(58) Field of Classification Search ............ 356/73, 356/445, 301; 250/339.11
See application file for complete search history.

(56) References Cited

U.S. PATENT DOCUMENTS

| 4,602,869 A | 7/1986 | Harrick |
| 4,975,581 A | 12/1990 | Robinson et al. |
| 5,153,675 A | 10/1992 | Beauchaine |

(Continued)

FOREIGN PATENT DOCUMENTS

EP 1 560 058 8/2005

(Continued)

OTHER PUBLICATIONS

N.J. Harrick et al., "Advances in Optical Spectroscopy: The Ultra-Small Sample Analyzer", Applied Spectroscopy 45(6): 944-948 (1991).

(Continued)

*Primary Examiner* — Layla Lauchman
(74) *Attorney, Agent, or Firm* — Gordon Stewart

(57) ABSTRACT

We disclose apparatus that includes: (a) an enclosure including an aperture; (b) a prism mounted in the enclosure so that a surface of the prism is exposed through the aperture; (c) an optical assembly contained within the enclosure, the optical assembly including a radiation source and a radiation detector, the source being configured to direct radiation towards the prism and the detector being configured to detect radiation from the source reflected from the exposed surface of the prism; and (d) an electronic processor contained within the enclosure, the electronic processor being in communication with the detector. The apparatus can be configured so that, during operation, the electronic processor determines information about a sample placed in contact with the exposed surface of the prism based on radiation reflected from the exposed prism surface while it is in contact with the sample.

15 Claims, 10 Drawing Sheets

U.S. PATENT DOCUMENTS

| | | | |
|---|---|---|---|
| 5,200,609 | A | 4/1993 | Sting et al. |
| 5,452,716 | A * | 9/1995 | Clift .................... 600/373 |
| 5,534,698 | A | 7/1996 | Ohshima et al. |
| 5,569,921 | A | 10/1996 | Sato et al. |
| 5,714,758 | A | 2/1998 | Neu |
| 5,991,029 | A | 11/1999 | Doyle |
| 6,031,233 | A | 2/2000 | Levin et al. |
| 6,141,100 | A | 10/2000 | Burka et al. |
| 6,445,938 | B1 | 9/2002 | Berman et al. |
| 6,507,396 | B1 | 1/2003 | Godfried et al. |
| 6,654,125 | B2 | 11/2003 | Maynard et al. |
| 6,919,959 | B2 | 7/2005 | Masten |
| 7,034,944 | B2 | 4/2006 | Rapp et al. |
| 7,047,810 | B2 | 5/2006 | Kogan et al. |
| 7,057,791 | B2 | 6/2006 | Azimi et al. |
| 7,062,133 | B2 | 6/2006 | Azimi et al. |
| 7,068,905 | B2 | 6/2006 | Vakhshoori et al. |
| 7,099,004 | B2 | 8/2006 | Masten |
| 7,110,109 | B2 | 9/2006 | Knopp et al. |
| 7,113,814 | B2 | 9/2006 | Ward et al. |
| 7,180,653 | B2 | 2/2007 | Knopp et al. |
| 7,190,861 | B2 | 3/2007 | Knopp et al. |
| 7,215,836 | B2 | 5/2007 | Vakhshoori et al. |
| 7,254,501 | B1 | 8/2007 | Brown et al. |
| 7,289,208 | B2 | 10/2007 | Vakhshoori et al. |
| 7,302,136 | B2 | 11/2007 | Vakhshoori et al. |
| 7,344,905 | B2 | 3/2008 | Wang et al. |
| 7,362,423 | B2 | 4/2008 | Masten |
| 7,409,125 | B2 | 8/2008 | Azimi et al. |
| 7,417,731 | B1 | 8/2008 | Masten |
| 7,420,672 | B2 | 9/2008 | Wang et al. |
| 7,499,159 | B2 | 3/2009 | Knopp et al. |
| 7,675,611 | B2 * | 3/2010 | Azimi et al. .................... 356/73 |
| 7,928,391 | B2 | 4/2011 | Azimi et al. |
| 8,081,305 | B2 | 12/2011 | Azimi et al. |
| 2002/0149777 | A1 | 10/2002 | Schreiber |
| 2004/0267166 | A1 * | 12/2004 | Ooshima et al. .............. 600/590 |
| 2005/0225758 | A1 | 10/2005 | Knopp et al. |
| 2005/0229698 | A1 * | 10/2005 | Beecroft et al. ................ 73/300 |
| 2005/0248759 | A1 | 11/2005 | Wang et al. |
| 2006/0045151 | A1 | 3/2006 | Vakhshoori et al. |
| 2006/0088069 | A1 | 4/2006 | Vakhshoori et al. |
| 2006/0170917 | A1 | 8/2006 | Vakhshoori et al. |
| 2007/0002319 | A1 | 1/2007 | Knopp et al. |
| 2007/0058243 | A1 | 3/2007 | Vakhshoori et al. |
| 2007/0074574 | A1 | 4/2007 | Kogan et al. |
| 2007/0091412 | A1 | 4/2007 | Azimi et al. |
| 2007/0116069 | A1 | 5/2007 | Wang et al. |
| 2007/0125950 | A1 | 6/2007 | Wang et al. |
| 2007/0194239 | A1 | 8/2007 | McAllister et al. |
| 2008/0033663 | A1 | 2/2008 | Brown et al. |
| 2008/0069169 | A1 | 3/2008 | Wang et al. |
| 2008/0170223 | A1 | 7/2008 | Vakhshoori et al. |
| 2008/0291426 | A1 | 11/2008 | Azimi et al. |
| 2009/0010597 | A1 | 1/2009 | Azimi et al. |
| 2009/0014646 | A1 | 1/2009 | Vakhshoori et al. |
| 2009/0033928 | A1 | 2/2009 | Azimi et al. |
| 2009/0057422 | A1 | 3/2009 | Dugas et al. |
| 2009/0213361 | A1 | 8/2009 | Rhodes et al. |

FOREIGN PATENT DOCUMENTS

JP        04-186140 A  *  7/1992

OTHER PUBLICATIONS

A.R. Korb et al., "Portable Fourier transform infrared spectroradiometer for field measurements of radiance and emissivity", Applied Optics 35(10): 1679-1692 (1996).

High Pressure Diamond Optics, Inc., "M-A-II", http://hpdo.com/ma2.html, Dec. 4, 2008 (5 pages).

* cited by examiner

HANDHELD INFRARED AND RAMAN MEASUREMENT DEVICES AND METHODS

CROSS-REFERENCE TO RELATED APPLICATIONS

Pursuant to 35 U.S.C. §120, this application is a continuation of and claims the benefit of prior U.S. application Ser. No. 12/691,047, filed on Jan. 21, 2010, now U.S. Pat. No. 7,928,391 which is a continuation of and claims the benefit of prior U.S. application Ser. No. 11/864,304, now U.S. Pat. No. 7,675,611, filed on Sep. 28, 2007, which claims priority to U.S. Provisional Application No. 60/931,086, filed on May 21, 2007. The entire contents of each of the prior applications are incorporated herein by reference.

TECHNICAL FIELD

This disclosure relates to optical measurement and identification of samples.

BACKGROUND

Optical measurement devices can be used by security personnel to identify unknown substances that may potentially pose a threat to public safety. For example, infrared radiation can be used to interrogate and identify the unknown substances.

SUMMARY

In general, in a first aspect, the disclosure features an apparatus that includes: (a) a enclosure including an aperture; (b) a prism mounted in the enclosure so that a surface of the prism is exposed through the aperture; (c) an optical assembly contained within the enclosure, the optical assembly including a radiation source and a radiation detector, the source being configured to direct radiation towards the prism and the detector being configured to detect radiation from the source reflected from the exposed surface of the prism; and (d) an electronic processor contained within the enclosure, the electronic processor being in communication with the detector. The apparatus is configured so that, during operation, the electronic processor determines information about a sample placed in contact with the exposed surface of the prism based on radiation reflected from the exposed prism surface while it is in contact with the sample.

Embodiments of the apparatus can include one or more of the following features.

The enclosure can have a hand-held form factor. A maximum dimension of the enclosure can be less than 30 cm. A total mass of the apparatus can be less than 2 kg.

The apparatus can be an infrared spectrometer. For example, the apparatus can be a Fourier-transform infrared spectrometer.

The enclosure can be formed of a plastic material.

The enclosure can include a plurality of shock-absorbing external protrusions. The shock-absorbing protrusions can be formed of an elastic material. The elastic material can include rubber.

The enclosure can be a first enclosure, and the first enclosure can include a second enclosure positioned within the first enclosure, the second enclosure including the optical assembly and being hermetically sealed with respect to the first enclosure.

The enclosure can be a rugged enclosure configured to protect components of the apparatus contained within the enclosure.

The apparatus can include a support apparatus configured to connect to the enclosure. The support apparatus can include a sample region configured to support a sample. The sample region can include alignment marks for orienting the sample. The support apparatus can be configured to position the prism proximal to the sample region when the enclosure is connected to the support apparatus. The support apparatus can be configured to permit translation of the enclosure in a direction perpendicular to a plane in which the sample region extends. The support apparatus can be configured to permit translation of the enclosure so that the prism contacts a sample positioned in the sample region.

The support apparatus can be formed of a plastic material. The support apparatus can include a first member that includes the sample region, and a second member that includes an attachment mechanism configured to connect to the enclosure. The first and second members can be joined by a hinge. The support apparatus can be folded by rotating the one of the first and second members about an axis of the hinge relative to the other member. The support apparatus can be collapsible.

The aperture can include a protrusion formed in a wall of the enclosure. The protrusion can include a liquid-proof seal to prevent fluids from entering the enclosure through the aperture. The protrusion can include a mounting plate configured to support the prism. The prism can be attached to the mounting plate by soldering. The prism can be attached to the mounting plate by brazing. The mounting plate can include a metal (e.g., stainless steel, Hastelloy).

A surface of the prism that attaches to the mounting plate can include a coating. The coating can include gold.

The protrusion can extend outward from the enclosure a distance of 10 mm or more. The protrusion can extend outward from the enclosure a distance of 100 mm or less.

The protrusion can include a support member configured to support an edge of the prism that is not attached to the mounting plate. The edge can be positioned opposite to the exposed surface of the prism.

The prism can include a chemically inert material (e.g., diamond).

The prism can be positioned within the aperture so that during operation, incident electromagnetic radiation enters the prism through a first prism surface and reflects from the exposed surface. The prism can be positioned within the aperture so that electromagnetic radiation reflected from the exposed surface leaves the prism through a second prism surface different from the first prism surface.

A maximum dimension of the exposed surface is 10 mm or less (e.g., 3 mm or less, 1 mm or less).

The exposed surface can include a coating. The coating can include gold.

The exposed surface can be substantially planar.

An area of the exposed surface can be 300 mm$^2$ or less (e.g., 20 mm$^2$ or less).

The radiation source can include one or more laser diodes. Alternatively, or in addition, the radiation source can include one or more light-emitting diodes. Alternatively, or in addition, the radiation source comprises one or more lasers.

The radiation directed by the source towards the prism can include infrared radiation.

The radiation directed by the source towards the prism can include a distribution of radiation wavelengths, and a center wavelength of the distribution can be 750 nm or more (e.g., 900 nm or more, 1100 nm or more). The radiation directed by the source towards the prism can have an intensity of 100 mW/mm$^2$ or more (e.g., 300 mW/mm$^2$ or more).

A path length of the radiation within the prism can be 10 mm or less (e.g., 3 mm or less, 1 mm or less).

Radiation produced by the source can be incident on a beamsplitter prior to reaching the prism. The beamsplitter can include a beamsplitting optical element and a phase compensating plate.

The beamsplitter can be configured to direct a first beam of radiation to a first reflector, and to direct a second beam of radiation to second reflector. The first reflector can be configured to receive the first radiation beam traveling along a first radiation path, and to direct the first radiation beam toward the beamsplitter along a direction that is substantially parallel to the first radiation path. The second reflector can be configured to receive the second radiation beam traveling along a second radiation path, and to direct the second radiation beam toward the beamsplitter along a direction that is substantially parallel to the second radiation path. The beamsplitter can be configured to receive the reflected first and second radiation beams, to spatially overlap the reflected first and second radiation beams, and to direct the spatially overlapped beams toward the prism.

The second reflector can include a first reflecting surface configured to reflect the second radiation beam, and a second reflecting surface positioned opposite the first reflecting surface. The first reflecting surface can include a first material, and the second reflecting surface can include a second material different from the first material. The second reflecting surface can be a portion of an interferometer. The interferometer can be a Michelson interferometer. The interferometer can include a detector configured to measure a position of the second reflector.

The apparatus can include a translation mechanism coupled to the second reflector and configured to translate the second reflector in a direction substantially parallel to the second radiation path. The translation mechanism can include a member connected to the second reflector, and a sleeve surrounding the member, wherein the member is movable relative to the sleeve in a direction substantially parallel to the second radiation path. The member and the sleeve can include zirconia. Alternatively, or in addition, the member and the sleeve can include aluminum oxide and/or silicon carbide and/or steel and/or glass. A fluid (e.g., silicone oil) can be disposed between the member and the sleeve. The apparatus can include a device in communication with the electronic processor and configured to translate the member relative to the sleeve.

The apparatus can include a coating disposed on an inner surface of the enclosure between the inner surface of the enclosure and the optical assembly. The coating can include silicone rubber. A thickness of the coating can be 1.0 mm or more.

The apparatus can include an electronic display.

The apparatus can include a communication interface configured to permit communication with one or more devices over a communication link. The communication interface can include a data transmitter and a data receiver. The data transmitter and data receiver can be configured to permit communication over a communication link that includes a network. Alternatively, or in addition, the data transmitter and data receiver can be configured to permit communication over a communication link that includes a direct connection to one or more devices. The data transmitter and data receiver can be configured to permit communication through a secure connection to one or more devices over the communication link.

The data transmitter and data receiver can be configured to transmit and receive data wirelessly.

The electronic processor can be configured to receive data that is transmitted by one or more devices and received by the data receiver. The data can include reference information about one or more substances.

The apparatus can include a storage medium configured to store reference information about one or more substances. The storage medium can include a magnetic storage medium. The storage medium can be removable from the enclosure. The reference information can include infrared absorption information and/or Raman scattering information and/or a list of prohibited substances. The storage medium can be configured to receive updated reference information from one or more devices over a communication link.

The radiation detector can be a pyroelectric detector. The radiation detector can be a photoelectric detector. The radiation detector can be a photodiode.

The information about the sample can include sample information, and the electronic processor can be configured to compare the sample information to reference information. The electronic processor can be configured to retrieve the reference information from a storage medium prior to comparing the sample and reference information. The sample information and reference information can include infrared absorption information.

The processor can be configured to apply a mathematical transformation to the sample information prior to the comparing, where the transformation transforms the sample information from a first measurement domain to a second measurement domain. The transformation can be a Fourier transformation.

The electronic processor can be configured to determine an identity of the sample based on the comparison. Determining an identity can include determining that the sample information corresponds to reference information for a particular substance. The processor can be configured to output a signal to an electronic display based on the comparison. The signal can indicate to a human operator that the sample information does not correspond to reference information available to the electronic processor. The signal can indicate to a human operator that the sample information corresponds to reference information for a particular substance. The signal can include a quantitative metric that corresponds to a measurement of a correspondence between the sample information and the reference information.

The signal can include a colored region on the electronic display.

The processor can be configured to output an audio signal based on the comparison.

The signal can indicate an alarm condition or a no-alarm condition. The no-alarm condition can correspond to the substance not appearing on a list of prohibited substances. The alarm condition can correspond to the substance appearing on a list of prohibited substances.

The information about the sample can include an interferometric signal measured by the radiation detector. Variations in the interferometric signal can correspond in part to absorption by the sample of radiation generated by the radiation source.

The electronic processor can be configured to make multiple measurements of information about the sample, at least some of the multiple measurements corresponding to different positions of the second reflector. A maximum difference among the different positions of the second reflector can be 2 mm or more (e.g., 5 mm or more).

The electronic processor can be configured to obtain a first identity of the sample that is determined based on Raman scattering information about the sample, and to compare the first identity to a second identity of the sample that is determined based on the comparison between the sample and reference information. The first identity can be obtained from a device configured to measure Raman scattering information about the sample. The first identity can be obtained over a communication link.

The electronic processor can be configured to obtain Raman scattering information about the sample, and to compare the sample Raman scattering information to reference Raman scattering information. The electronic processor can be configured to retrieve the reference Raman scattering information from a storage medium prior to comparing the sample Raman scattering information and the reference Raman scattering information. The electronic processor can be configured to determine an identity of the sample based on the comparison between the sample and reference information, and based on the comparison between the sample and reference Raman scattering information. The Raman scattering information about the sample can be obtained from another device over a communication link.

The radiation source can be a first radiation source and the radiation detector can be a first radiation detector, and the apparatus can include a second radiation source configured to direct radiation to be incident on the sample, and a second radiation detector configured to detect radiation scattered from the sample. The radiation provided by the second radiation source can pass through the exposed surface of the prism prior to being incident on the sample.

The aperture can include a first aperture, and the apparatus can include a second aperture, the radiation provided by the second radiation source passing through the second aperture prior to being incident on the sample.

The radiation provided by the second radiation source can include a distribution of radiation wavelengths, where a center wavelength of the distribution is 400 nm or less (e.g., 350 nm or less). An intensity of the radiation provided by the second radiation source can be 5 mW or less (e.g., 2 mW or less).

The second radiation source can include a laser diode.

The second detector can include a detector configured to measure radiation intensity at a plurality of different wavelengths. The second detector can include a Raman spectrometer.

The sample can include a solid (e.g,. a powder). Alternatively, or in addition, the sample can include a liquid and/or a gel. The sample can include a mixture of two or more substances.

Embodiments of the apparatus can also include any of the other features disclosed herein.

In another aspect, the disclosure features a method that includes positioning an exposed surface of a prism of a handheld measurement device so that the exposed surface contacts a sample, detecting electromagnetic radiation that interacts with the sample at the exposed surface of the prism and is reflected from the exposed surface, and determining information about the sample based on the detected radiation.

Embodiments of the method can include one or more of the following features.

The positioning can include grasping an enclosure of the measurement device, and supporting the enclosure to maintain contact between the exposed surface of the prism and the sample. The grasping can be performed by a system operator. The supporting can be performed by a system operator.

The supporting can include holding the enclosure with at least one hand. The supporting can include holding the enclosure with only one hand.

The method can include applying a force to the enclosure to cause the exposed surface of the prism to apply pressure to the sample.

The sample can be contacted only by the exposed surface of the prism prior to detecting electromagnetic radiation.

The sample may not be handled by a system operator prior to detecting electromagnetic radiation.

The method can include transmitting the information about the sample to another device over a communication link. The communication link can be a wireless communication link.

The method can include applying a mathematical transformation to the sample information. The mathematical transformation can include a Fourier transformation.

The method can include determining an identity of the sample based on the sample information. Determining an identity can include comparing the sample information to reference information stored in a storage unit.

Determining information about the sample can include measuring infrared absorption information about the sample. The method can include determining an identity of the sample based on the infrared absorption information about the sample.

Determining information about the sample can include obtaining Raman scattering information about the sample. The method can include determining an identity of the sample based on the infrared absorption information and the Raman scattering information about the sample. Obtaining Raman scattering information can include receiving Raman scattering information from a device over a communication link. Alternatively, or in addition, obtaining Raman scattering information can include measuring electromagnetic radiation scattered by the sample. The exposed surface of the prism can form a first aperture, and measuring electromagnetic radiation scattered by the sample can include measuring radiation received in a second aperture different from the first aperture. The electromagnetic radiation scattered by the sample can enter the prism through the exposed surface and can be detected after it leaves the prism.

Embodiments of the method can also include any of the other method steps disclosed herein, as appropriate.

Embodiments can include one or more of the following advantages.

The measurement devices disclosed herein include handheld Fourier transform infrared (FTIR) scanners that are robust and relatively simple to operate, so that operators with relatively limited training are capable of successfully using the devices. For example, embodiments of the measurement devices can include rugged housings which can prevent damage to internal components from rough handling, and/or a user interface which provides simple indicators that do not require specialized knowledge to interpret. Further, the devices can be automatically configured to alert additional (e.g., more highly-trained) personnel if hazardous substances are detected.

Measurement devices can be reliably and repeatably used in a variety of environments, including uncontrolled environments. For example, the measurement devices can be constructed in a way that facilitates ease of use and maintenance in uncontrolled environments. As an example, measurement devices can include a prism used to contact samples, and the prism can be sealed within a protrusion of the device's enclosure. The position of the prism relative to the enclosure permits the prism to be placed in contact with a sample during operation, and can allow a system operator to apply pressure to the sample. After completing a measurement of the sample, the position of the prism facilitates cleaning prior to testing of another sample. The seal prevents penetration of the sample into the enclosure, even when the sample is a fluid or gel.

Certain embodiment include moving mirrors. These mirrors can have high reflectivities for both sample measurement beams and position measurement beams, so that both sample information and mirror position information can be measured accurately and with high sensitivity. For example, a movable mirror within the measurement device can include a first reflecting surface from which a sample measurement beam reflects, and a second reflecting surface opposite the first reflecting surface from which a position-measuring beam reflects. By directing the position-measuring beam to reflect from a surface opposite the first surface, a reflective material or coating applied to the first reflecting surface can be chosen for a wavelength of the sample measurement beam, and a reflective material or coating applied to the second reflecting surface can be chosen for a wavelength of the position-measuring beam, which is different from the wavelength of the sample measurement beam.

Movable mirrors can be connected to a translation mechanism that provides for a relatively large range of motion of the mirror, and which prevents vibrational disturbances from perturbing the optical components of the measurement device. For example, the movable mirror can be connected to a shaft, and the shaft can be positioned within a bushing such that the shaft is movable relative to the bushing. A fluid can be positioned between the shaft and bushing to provide for smooth movement between shaft and bushing. The combination of the shaft and bushing permit movement of the mirror, and the shaft and bushing provide a significantly larger range of mirror movement than the range of movement permitted by leaf springs and similar devices. Further, the fluid decouples the shaft and bushing, so that mechanical disturbances (e.g., vibrations) are not coupled between the mirror and the rest of the optical assembly.

The measurement devices disclosed herein can also be relatively tolerant to a variety of environments, and to rough handling during deployment. For example, a vibration-damping material can be positioned between an inner wall of the enclosure and the optical assembly. The vibration-damping material dissipates mechanical disturbances that arise, for example, from handling of the enclosure by a system operator. The amplitude of such disturbances can be significantly reduced or eliminated by the vibration-damping material, so that the alignment of optical components within the enclosure is not disturbed.

The measurement devices can be configured to identify samples with a relatively high degree of certainty. For example, the measurement devices disclosed herein can be configured to identify samples based on both infrared absorption information and Raman scattering information. For certain samples, one type of information (e.g., Raman scattering information) can be used to confirm an identity of the sample that is determined using the other type of information (e.g., infrared absorption information). In this way, identification of samples can be performed with a higher degree of certainty than would generally be possible based on only one type of information. For some samples, Raman scattering information may provide relatively poor diagnostic information, and infrared absorption information can primarily be used to identify the sample. Conversely, for some samples, infrared absorption information may provide relatively poor diagnostic information, and Raman scattering information can primarily be used to identify the sample. In this manner, the infrared absorption information and Raman scattering information can be complementary to one another. The measurement devices can be configured to automatically determine whether to use only infrared absorption information, only Raman scattering information, or both types of information.

Unless otherwise defined, all technical and scientific terms used herein have the same meaning as commonly understood by one of ordinary skill in the art. Although methods and materials similar or equivalent to those described herein can be used in the practice or testing of the disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Many applications exist for portable measurement devices, including field identification of unknown substances by law enforcement and security personnel, detection of prohibited substances at airports and in other secure and/or public locations, and identification pharmaceutical agents, industrial chemicals, explosives, energetic materials, and other agents. To be useful in a variety of situations, it can be advantageous for portable measurement devices to have a handheld form factor and to rapidly provide accurate results.

In certain embodiments, the measurement devices and methods disclosed herein provide for contact between a sample of interest and the measurement device via a prism positioned in a protrusion of the measurement device's enclosure. The prism, which can be formed from a relatively hard material such as diamond, operates by ensuring that non-absorbed incident radiation is directed to a detector after undergoing total internal reflection within the prism. As a result, reflected radiation is coupled with high efficiency to the detector, ensuring sensitive operation of the measurement devices.

Samples of interest can be identified based on the reflected radiation that is measured by the detector. The reflected radiation can be used to derive infrared absorption information corresponding to the sample, and the sample can be identified by comparing the infrared absorption information to reference information for the sample that is stored in the measurement device. In addition to the identity of the sample, the measurement device can provide one or more metrics (e.g., numerical results) that indicate how closely the infrared absorption information matches the reference information. Further, the measurement device can compare the identity of the sample of interest to a list of prohibited substances—also stored within the measurement device—to determine whether particular precautions should be taken in handling the substance, and whether additional actions by security personnel, for example, are warranted. A wide variety of different samples can be interrogated, including solids, liquids, gels, powders, and various mixtures of two or more substances.

Figure 1:
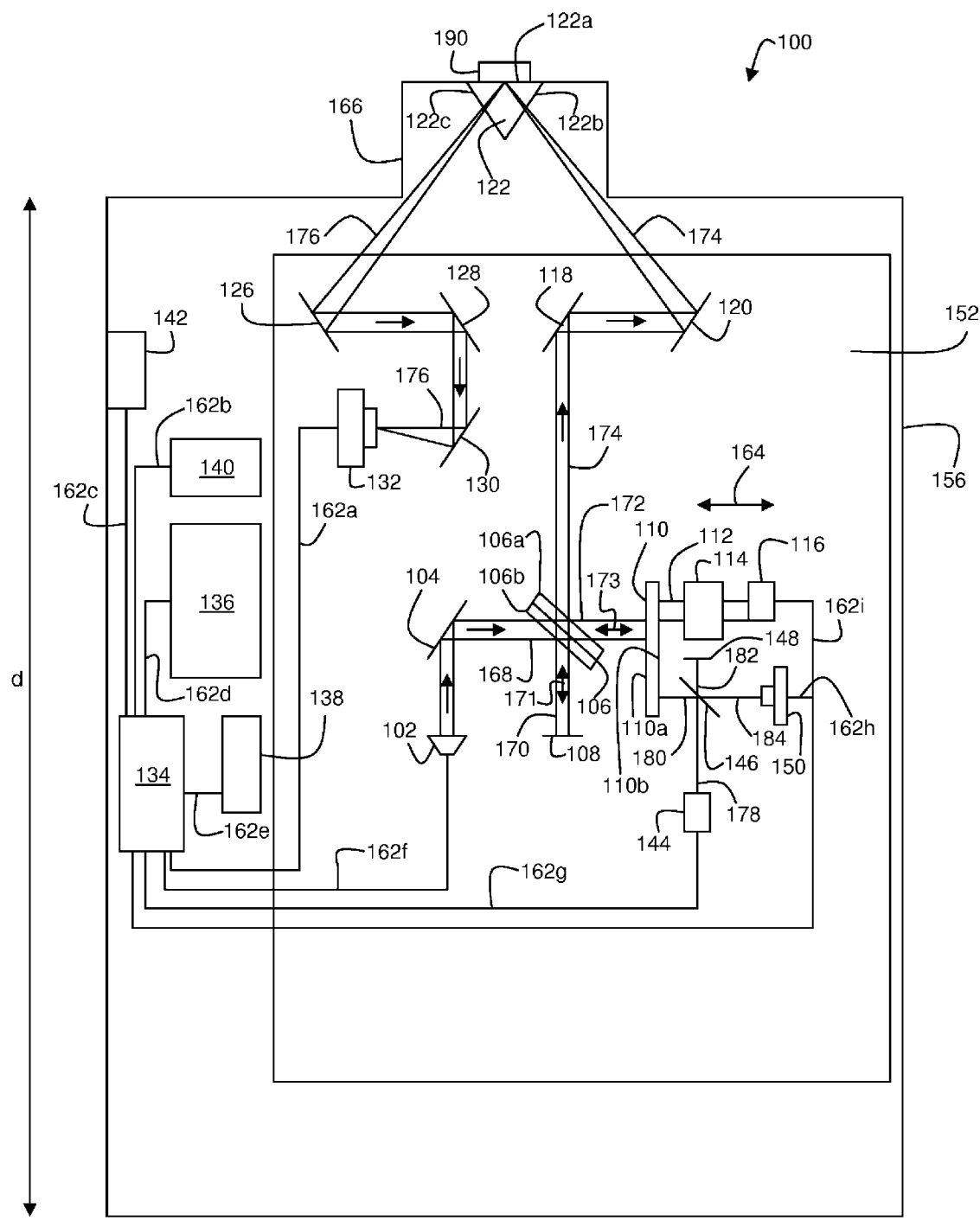
FIG. 1 is a schematic diagram of an embodiment of a measurement device.

FIG. 1 shows a schematic diagram of a measurement device 100. Device 100 includes an optical assembly mounted on an assembly support 152 that is fixed within an enclosure 156. The optical assembly includes: radiation sources 102 and 144; mirrors 104, 108, 110, 148, 118, 120, 126, 128, and 130; beamsplitters 106 and 146; detectors 132 and 150; and prism 122. Device 100 also includes a shaft 112, a bushing 114, and an actuator 116 coupled to mirror 110, and an electronic processor 134, an electronic display 136 (e.g., including a flat panel display element such as a liquid crystal display element, an organic light-emitting diode display element, an electrophoretic display element, or another type of display element), an input device 138, a storage unit 140, and a communication interface 142. Electronic processor 134 is in electrical communication with detector 132, storage unit 140, communication interface 142, display 136, input device 138, radiation sources 102 and 144, detector 150, and actuator 116, respectively, via communication lines 162a-i.

Measurement device 100 is configured for use as a Fourier transform infrared (FTIR) spectrometer. During operation, radiation 168 is generated by radiation source 102 under the control of processor 134. Radiation 168 is directed by mirror 104 to be incident on beamsplitter 106, which is formed from a beamsplitting optical element 106a and a phase compensating plate 106b, and which divides radiation 168 into two beams. A first beam 170 reflects from a surface of beamsplitter 106, propagates along a beam path which is parallel to arrow 171, and is incident on fixed mirror 108. Fixed mirror 108 reflects first beam 170 so that first beam 170 propagates along the same beam path, but in an opposite direction (e.g., towards beamsplitter 106).

A second beam 172 is transmitted through beamsplitter 106 and propagates along a beam path which is parallel to arrow 173. Second beam 172 is incident on a first surface 110a of movable mirror 110. Movable mirror 110 reflects second beam 172 so that beam 172 propagates along the same beam path, but in an opposite direction (e.g., towards beamsplitter 106).

First and second beams 170 and 172 are combined by beamsplitter 106, which spatially overlaps the beams to form incident radiation beam 174. Mirrors 118 and 120 direct incident radiation beam 174 to enter prism 122 through prism surface 122b. Once inside prism 122, radiation beam 174 is incident on surface 122a of the prism 122. Surface 122a of prism 122 is positioned such that it contacts a sample of interest 190. When radiation beam 174 is incident on surface 122a, a portion of the radiation is coupled into sample 190 through surface 122a. Typically, for example, sample 190 absorbs a portion of the radiation in radiation beam 174.

Radiation beam 174 undergoes total internal reflection from surface 122a of prism 122 as reflected beam 176. Reflected beam 176 includes, for example, the portion of incident radiation beam 174 that is not absorbed by sample 190. Reflected beam 176 leaves prism 122 through surface 122c, and is directed by mirrors 126, 128, and 130 to be incident on detector 132. Under the control of processor 134, detector 132 measures one or more properties of the reflected radiation in reflected beam 176. For example, detector 132 can determine absorption information about sample 190 based on measurements of reflected beam 176.

Typically, the radiation in reflected beam 176 is measured at a plurality of positions of movable mirror 110. Mirrors 108 and 110, together with beamsplitter 106, are arranged to form a Michelson interferometer, and by translating mirror 110 in a direction parallel to arrow 164 prior each measurement of reflected radiation 176, the plurality of measurements of the radiation in reflected beam 176 form an interferogram. The interferogram includes information such as sample absorption information. Processor 134 can be configured to apply one or more mathematical transformations to the interferogram to obtain the sample absorption information. For example, processor 134 can be configured to transform the interferogram measurements from a first domain (such as time or a spatial dimension) to a second domain (such as frequency) that is conjugate to the first domain. The transform(s) that is/are applied to the data can include a Fourier transform, for example.

Movable mirror 110 is coupled to shaft 112, bushing 114, and actuator 116. Shaft 112 moves freely within bushing 114, and a viscous fluid is disposed between shaft 112 and bushing 114 to permit relative motion between the two. Mirror 110 moves when actuator 116 receives control signals from processor 134 via communication line 162i. Actuator 116 initiates movement of shaft 112 in a direction parallel to arrow 164, and mirror 110 moves in concert with shaft 112. Bushing 114 provides support for shaft 112, preventing wobble of shaft 112 during translation. However, bushing 114 and shaft 112 are effectively mechanically decoupled from one another by the fluid disposed between them; mechanical disturbances such as vibrations are coupled poorly between shaft 112 and bushing 114. As a result, the alignment of the Michelson interferometer remains relatively undisturbed even when mechanical perturbations such as vibrations are present in other portions of device 100.

To measure the position of mirror 110, device 100 includes a second interferometer assembly that includes radiation source 144, beamsplitter 146, mirror 148, and detector 150. These components are arranged to form a Michelson interferometer. During a mirror position measurement operation, radiation source 144 receives a control signal from processor 134 via communication line 162g, and generates a radiation beam 178. Beam 178 is incident on beamsplitter 146, which separates radiation beam 178 into a first beam 180 and a second beam 182. First beam 180 reflects from the surface of beamsplitter 146 and is incident on a second surface 110b of mirror 110. Second surface 110b is positioned opposite first surface 110a of mirror 110. First beam 180 reflects from surface 110b and returns to beamsplitter 146.

Second beam 182 is transmitted through beamsplitter 146, reflected by mirror 148, and returned to beamsplitter 146. Beamsplitter 146 combines (e.g., spatially overlaps) reflected beams 180 and 182, and the combined beam 184 is directed to detector 150. Detector 150 receives control signals from processor 134 via communication line 162$h$, and is configured to measure an intensity of combined beam 184. As the position of mirror 110 changes (e.g., due to translation of mirror 110 along a direction parallel to arrow 164), the intensity of the radiation measured by detector 150 changes due to interference between first beam 180 and second beam 182 in combined beam 184. By analyzing the changes in measured radiation intensity from detector 150, processor 134 can determine with high accuracy the position of mirror 110.

Position information for mirror 110 is combined by processor 134 with measurements of the radiation in reflected beam 176 to construct an interferogram for sample 190. As discussed above, processor 134 can be configured to apply a Fourier transform to the interferogram to obtain absorption information about sample 190 from the interferogram. The absorption information can be compared by processor 134 to reference information (e.g., reference absorption information) stored in storage unit 140 to determine an identity of sample 190. For example, processor 134 can determine whether the absorption information for the sample matches any one or more of a plurality of sets of reference absorption information for a variety of substances that are stored as database records in storage unit 140. If a match is found (e.g., the sample absorption information and the reference information for a particular substance agree sufficiently), then sample 190 is considered to be identified by processor 134. Processor 134 can send an electronic signal to display 136 along communication line 162$d$ that indicates to a system operator that identification of sample 190 was successful, and provides the name of the identified substance. The signal can also indicate to the system operator how closely the sample absorption information and the reference information agree. For example, numeric values of one or more metrics can be provided which indicate the extent of correspondence between the sample absorption information and the reference information on a numerical scale.

If a match between the sample absorption information and the reference information is not found by processor 134, the processor can send an electronic signal to display 136 that indicates to the system operator that sample 190 was not successfully identified. The electronic signal can include, in some embodiments, a prompt to the system operator to repeat the sample absorption measurements.

Reference information stored in storage unit 140 can include reference absorption information for a variety of different substances, as discussed above. The reference information can also include one or more lists of prohibited substances. Lists of prohibited substances can include, for example, substances that passengers on commercial airline flights are not allowed to carry. Lists of prohibited substances can also include, for example, substances that are not permitted in various public locations such as government buildings for security and public safety reasons. If identification of sample 190 is successful, processor 134 can be configured to compare the identity of sample 190 against one or more lists of prohibited substances stored in storage unit 140. If sample 190 appears on a list as a prohibited substance, processor 134 can alert the system operator that a prohibited substance has been detected. The alert can include a warning message displayed on display 136 and/or a colored region (e.g., a red-colored region) on display 136. Processor 134 can also be configured to sound an audio alarm via a speaker to alert the system operator.

Storage unit 140 typically includes a re-writable persistent flash memory module. The memory module, which is removable from enclosure 156, is configured to store a database that includes a library of infrared absorption information about various substances. Processor 134 can retrieve reference absorption information from storage unit 140 via a request transmitted on communication line 162$b$. Storage unit 140 can also store device settings and other configuration information such as default operating parameters. Other storage media can also be included in storage unit 140, including various types of re-writable and non-rewritable magnetic media, optical media, and electronic memory.

Measurement device 100 also includes communication interface 142, which receives and transmits signals from/to processor 134 via communication line 162$c$. Communication interface 142 includes a wireless transmitter/receiver unit that is configured to transmit signals from processor 134 to other devices, and to receive signals from other devices and communicate the received signals to processor 134. Typically, for example, communication interface 142 permits processor 134 to communicate with other devices—including other measurement devices 100 and/or computer systems—via a wireless network that includes multiple devices connected to the network, and/or via a direct connection to another device. Processor 134 can establish a secure connection (e.g., an encrypted connection) to one or more devices to ensure that signals can only be transmitted and received by devices that are approved for use on the network.

Processor 134 communicates with a central computer system to update the database of reference information stored in storage unit 140. Processor 134 is configured to periodically contact the central computer system to receive updated reference information, and processor 134 can also receive automatic updates that are delivered by the central computer system. The updated reference information can include reference absorption information, for example, and can also include one or more new or updated lists of prohibited substances.

Processor 134 can also communicate with other measurement devices to broadcast alert messages when certain substances—such as substances that appear on a list of prohibited substances—are identified, for example. Alert messages can also be broadcast to one or more central computer systems. Alert information—including the identity of the substance, the location at which the substance was identified, the quantity of the substance, and other information—can also be recorded and broadcast to other measurement devices and computer systems.

In some embodiments, measurement device 100 can be connected to other devices over other types of networks, including isolated local area networks and/or cellular telephone networks. The connection can be a wireless connection or a wired connection. Signals, including alert messages, can be transmitted from processor 134 to a variety of devices such as cellular telephones and other network-enabled devices that can alert personnel in the event that particular substances (e.g., prohibited substances) are detected by measurement device 100.

Typically, input device 138 includes a control panel that enables a system operator to set configuration options and change operating parameters of measurement device 100. In some embodiments, measurement device 100 can also include an internet-based configuration interface that enables remote adjustment of configuration options and operating parameters. The interface can be accessible via a web browser, for example, over a secured or insecure network connection. The internet-based configuration interface permits remote updating of measurement device 100 by a central computer system or another device, ensuring that all measurement devices that are operated in a particular location or for a particular purpose have similar configurations. The internet-based interface can also enable reporting of device configurations to a central computer system, for example, and can enable tracking of the location of one or more measurement devices.

Radiation source 102 includes one or more laser diodes configured to provide infrared radiation, so that measurement device 100 functions as an infrared spectrometer. Typically, for example, the infrared radiation provided by source 102 includes a distribution of wavelengths, and a center wavelength of the distribution is about 785 nm. In general, radiation source 102 can include a variety of sources, including— in addition to laser diodes—light-emitting diodes and lasers. A center wavelength of the distribution of wavelengths of the radiation provided by source 102 can be 700 nm or more (e.g., 750 nm or more, 800 nm or more, 850 nm or more, 900 nm or more, 950 nm or more, 1000 nm or more, 1050 nm or more, 1100 nm or more, 1150 nm or more, 1200 nm or more, 1300 nm or more, 1400 nm or more).

Typically, an intensity of radiation 168 provided by source 102 is about 50 mW/mm$^2$. In general, however, the intensity of radiation 168 can be varied (e.g., via a control signal from processor 134 transmitted along communication line 162*f*) according to the particular sample 190 and the sensitivity of detector 132. In some embodiments, for example, the intensity of radiation 168 provided by source 102 is 10 mW/mm$^2$ or more (e.g., 25 mW/mm$^2$ or more, 50 mW/mm$^2$ or more, 100 mW/mm$^2$ or more, 150 mW/mm$^2$ or more, 200 mW/mm$^2$ or more, 250 mW/mm$^2$ or more, 300 mW/mm$^2$ or more, 400 mW/mm$^2$ or more).

In certain embodiments, the properties of radiation 168 provides by source 102 can be altered by control signals from processor 134. For example, processor 134 can adjust an intensity and/or a spectral distribution of radiation 168. Processor 134 can adjust spectral properties of radiation 168 by activating one or more filter elements (not shown in FIG. 1), for example. In general, measurement device 100 can include lenses, mirrors, beamsplitters, filters, and other optical elements that can be used to condition and adjust properties of radiation 168.

Detector 132 is configured to measure reflected radiation beam 176 after the beam leaves prism 122. Typically, detector 132 includes a pyroelectric detector element that generates an electronic signal, the magnitude of the signal being dependent on an intensity of radiation beam 176. In general, however, detector 132 can include a variety of other detection elements. For example, in some embodiments, detector 132 can be a photoelectric detector (e.g., a photodiode) that generates an electronic signal with a magnitude that depends on the intensity of radiation beam 176.

Radiation source 144 generates radiation beam 178 that is used to measure the position of mirror 110. Radiation source 144 includes a vertical cavity surface-emitting laser (VCSEL) that generates radiation having a central wavelength of 850 nm. In general, radiation source 144 can include a variety of sources, including laser diodes, light-emitting diodes, and lasers. Radiation beam 178 can have a central wavelength in an ultraviolet region, a visible region, or an infrared region of the electromagnetic spectrum. For example, in some embodiments, a central wavelength of radiation beam 178 is between 400 nm and 1200 nm (e.g., between 400 nm and 500 nm, between 500 nm and 600nm, between 600 nm and 700 nm, between 700 nm and 800 nm, between 800 nm and 900 nm, between 900 nm and 1000 nm, between 1000 nm and 1100 nm, between 1100 nm and 1200 nm).

Detector 150 can include a variety of different detection elements configured to generate an electronic signal in response to beam 184. In some embodiments, for example, detector 184 includes a pyroelectric detector. In certain embodiments, detector 184 includes a photoelectric detector, such as a photodiode. Generally, any detection element that generates an electronic signal that is sensitive to changes in an intensity of beam 184 can be used in detector 150.

Figure 2:
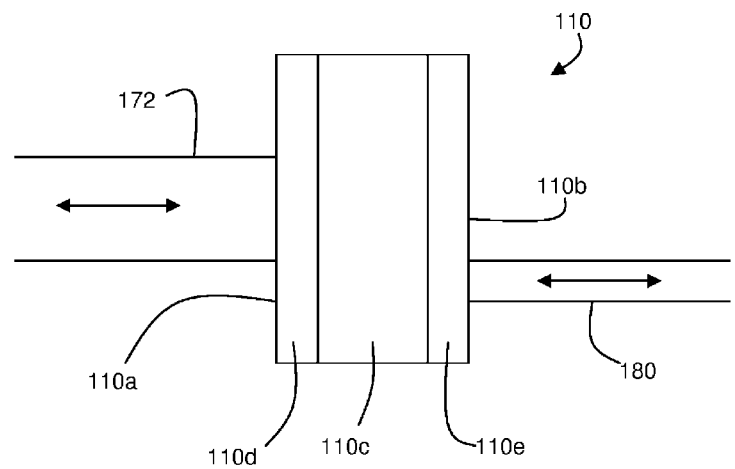
FIG. 2 is a schematic diagram of an embodiment of an interferometer mirror.

As shown in FIG. 1, mirror 110 includes two opposite reflecting surfaces 110*a* and 110*b*. An enlarged schematic diagram of mirror 110 is shown in FIG. 2. Mirror 110 includes a substrate 110*c* (formed of glass or fused silica, for example), with a first coating 110*d* disposed on substrate 110*c* to form first reflecting surface 110*a*, and a second coating 110*e* disposed on an opposite surface of substrate 110*c* to form second reflecting surface 110*e*. Typically, beams 172 and 180, which are incident on surfaces 110*a* and 110*b* of mirror 110, respectively, have different central wavelengths. The materials that form first coating 110*d* and second coating 110*e* are selected to provide high reflectivity for beams 172 and 180. In some embodiments, depending on the central wavelengths of beams 172 and 180, a single coating material with high reflectivity at both central wavelengths is used to form coatings 110*d* and 110*e*. In certain embodiments, two different materials are used to form coatings 110*d* and 110*e*, where each coating material is selected to provide high reflectivity of beam 172 or beam 180, as appropriate.

The use of two different coating materials—each selected to provide high reflectivity for a beam having a particular central wavelength—provides an advantage over conventional position-measuring interferometer systems. In certain conventional systems, for example, beams 172 and 180 reflect from a common surface of mirror 110 (e.g., surface 110*a*). If beams 172 and 180 have central wavelengths that differ appreciably, then it is difficult to find a material for coating 110*d* that has very high reflectivity for both beams. As a result, one or even both of beams 172 and 180 is reduced in intensity due to reflection losses from mirror 110.

Shaft 112 and bushing 114 permit smooth, vibration-decoupled motion of mirror 110 in a direction parallel to arrow 164 (e.g., in a direction parallel to the optical path of beam 172). In the embodiment shown in FIG. 1, both shaft 112 and bushing 114 are substantially cylindrical, and bushing 114 has a central bore adapted to receive shaft 112. In general, however, shaft 112 can be replaced by any member that is connected to mirror so that the member moves together with mirror 110. Similarly, bushing 114 can, in general, include any sleeve or other member that is adapted to receive shaft 112, and configured to permit motion of shaft 112 and mirror 110 relative to bushing 114.

Shaft 112 and bushing 114 can generally be formed from the same material, or from different materials. Typically, shaft 112 and bushing 114 are formed from hard, smooth materials. Exemplary materials that can be used to form shaft 112 and/or bushing 114 include, but are not limited to, zirconia, aluminum oxide, silicon carbide, steel, and/or glass.

As discussed above, a fluid is disposed between shaft 112 and bushing 114. Typically, the fluid is a viscous fluid that permits relatively friction-free movement of shaft 112 relative to bushing 114. The fluid also decouples shaft 112 and bushing 114, so that mechanical disturbances in one of these elements (e.g., bushing 114) are not effectively transmitted to the other element (e.g., shaft 112). The fluid therefore ensures that many of the optical elements—and mirror 110 in particular—of measurement device 100 are not significantly disturbed by mechanical perturbations. A variety of different fluids can be used between shaft 112 and bushing 114 including, for example, silicone oil.

The overall translation mechanism that is configured to translate mirror 110 includes shaft 112, bushing 114, and actuator 116. Actuator 116 is coupled to shaft 112 and, on receiving suitable control signals from processor 134, translates mirror 110 in a direction parallel to the optical path of beam 172 by applying a force to shaft 112. Due to the applied force, shaft 112 moves relative to bushing 114, causing translation of mirror 110. Typically, actuator 116 includes a coil winding that is configured to generate a magnetic field when a control signal is received. The magnetic field produces an attractive or repulsive force between actuator 116 and bushing 114 (which can be formed from a metal and/or magnetic material, for example), causing translational motion of actuator 116 and coupled shaft 112 relative to bushing 114. In general, many different types of actuators can be used to translate mirror 110. Exemplary alternative actuators include voice coil actuators, stepper motors, flexure-based translation stages, and piezoelectric devices.

Measurement device 100 is generally configured to make multiple measurements of infrared absorption information from sample 190 to construct an interferogram. Typically, for example, each of the multiple measurements corresponds to a different position of mirror 110 along an axis parallel to the beam path of beam 172. In certain embodiments, a maximum difference among the different positions of mirror 110 is 0.5 mm or more (e.g., 1 mm or more, 2 mm or more, 3 mm or more, 4 mm or more, 5 mm or more, 7 mm or more, 10 mm or more).

As discussed above, during operation, prism 122 is placed in contact with sample 190. Radiation is incident on surface 122a of prism 122 that contacts sample 190, and a portion of the incident radiation couples into sample 190 where it is absorbed. The remaining radiation undergoes total internal reflection from surface 122a of prism 122, and is detected by a suitable detector 132. To contact sample 190, prism 122 is positioned in an aperture than includes a protrusion 166 formed in a wall of enclosure 156. Typically, protrusion 166 includes a liquid-proof seal to prevent sample fluid from entering enclosure 156 when prism 122 contacts a liquid sample 190.

Figure 3:
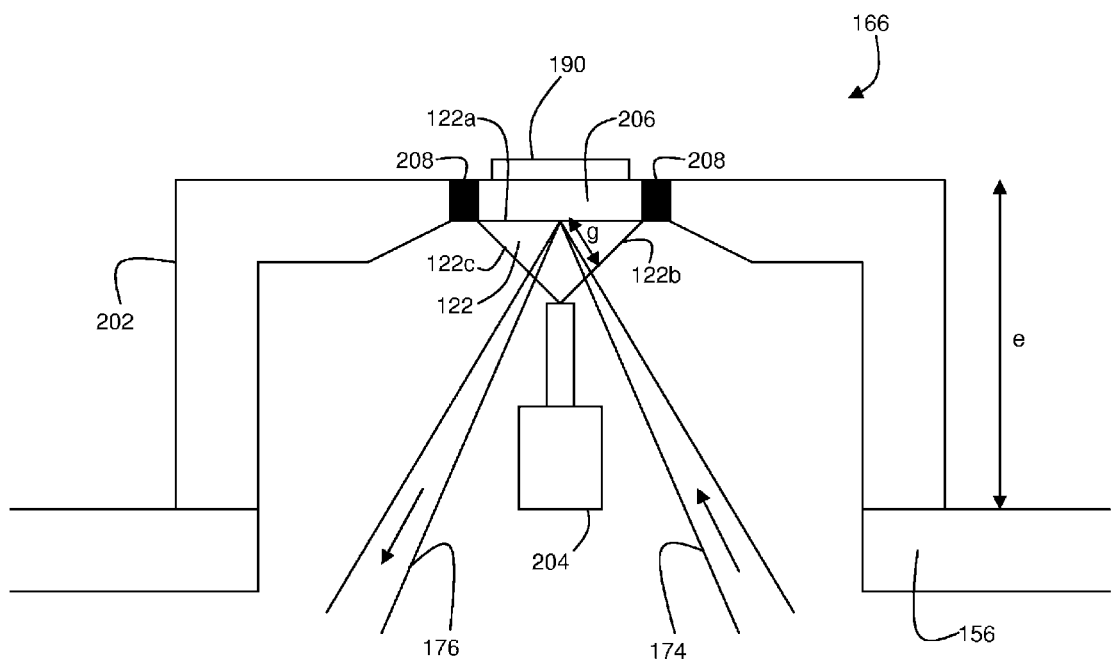
FIG. 3 is a schematic diagram of an embodiment of an aperture.

FIG. 3 shows an enlarged schematic view of the aperture including protrusion 166. Prism 122 includes a surface 122a that is positioned to contact sample 190. Radiation enters prism 122 through surface 122b, and leaves prism 122 through surface 122c. Surface 122a includes a coating 206.

An edge of prism 122 opposite to surface 122a is supported from below by a prism base 204. Surface 122a of prism 122 is also attached to mounting plate 202 to provide support to prism 122 from above. Support provided by plate 202 and base 204 allows prism 122 to withstand significant applied forces during operation without being displaced from its mounting position within protrusion 166. During operation, a system operator can position measurement device 100 so that prism 122 (e.g., surface 122a) contacts sample 190, and the operator can apply a force to enclosure 156 so that prism 122 exerts a compressive force on sample 190. This can improve a signal-to-noise ratio in measurements of reflected radiation beam 176, and can enable measurement of certain samples which would otherwise yield inconclusive results in the absence of direct contact with prism 122 and/or the application of compressive force to sample 190. Support base 204 and mounting plate 202 ensure that prism 122 remains in the same position within protrusion 166 during application of these forces.

Mounting plate 202 and support base 204 can be formed from the same or different materials. Typically, for example, mounting plate 202 and support base 204 include one or more metals. Exemplary materials from which either or both of mounting plate 202 and support base 204 can be formed include stainless steel and Hastelloy.

As discussed above, surface 122a of prism 122 includes a coating 206. Coating 206 can include one or more metals such as, for example, gold. A metal coating 206 permits attachment of surface 122a to mounting plate 202 via soldering, welding, or brazing. In FIG. 3, prism 122 is soldered to mounting plate 202 via solder joints 208 between mounting plate 202 and coating 206.

To withstand physical handling during measurement and chemical attack by samples, prism 122 is typically formed from a hard, chemically inert material. Prism 122 is also configured to provide for total internal reflection of radiation beam 174, and so prism 122 is typically formed from a relatively high refractive index material. Materials that can be used to form prism 122 include naturally occurring and synthetic diamond, for example.

Protrusion 166 extends outward for a distance e from enclosure 156. The extension of protrusion 166 permits contact between sample 190 and surface 122a of prism 122, and at the same time prevents contact between sample 190 and the rest of measurement device 100. In general, the distance e can be selected according to the type and environment of the samples of interest. In some embodiments, for example, e can be 10 mm or more (e.g., 20 mm or more, 30 mm or more, 40 mm or more) and/or 100 mm or less (e.g., 90 mm or less, 80 mm or less, 70 mm or less, 60 mm or less).

Figure 4:
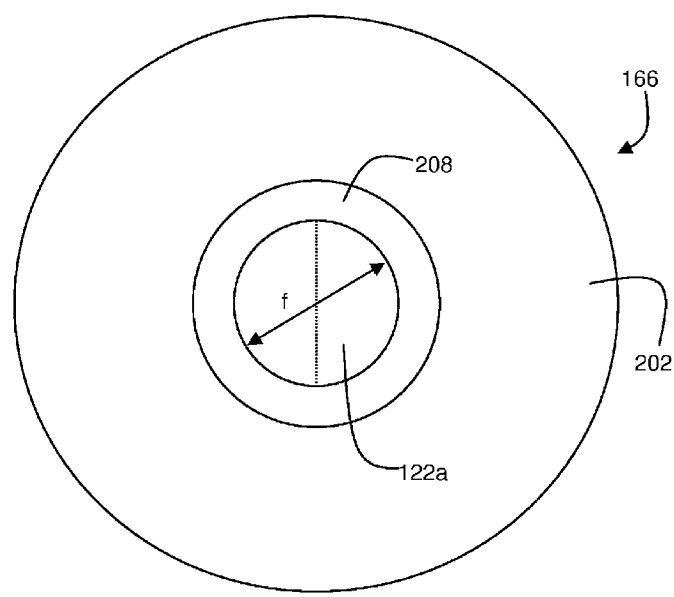
FIG. 4 is a plan view of an embodiment of an aperture.

FIG. 4 shows a plan view of the aperture that includes protrusion 166. In the embodiment shown, surface 122a of prism 122 has a substantially circular cross-sectional shape. In general, however, prism 122 can have a variety of different cross-sectional shapes, including ellipsoidal, rectangular, triangular, square, and irregular.

Surface 122a of prism 122, which is substantially planar in the embodiment shown in FIG. 4, has a maximum dimension f. In certain embodiments, f can be 10 mm or less (e.g., 9 mm or less, 8 mm or less, 7 mm or less, 6 mm or less, 5 mm or less, 4 mm or less, 3 mm or less, 2 min or less, 1 mm or less, 0.5 mm or less). In some embodiments, an area of surface 122a can be 500 $mm^2$ or less (e.g., 400 $mm^2$ or less, 300 $mm^2$ or less, 200 $mm^2$ or less, 100 $mm^2$ or less, 50 $mm^2$ or less, 30 $mm^2$ or less, 20 $mm^2$ or less, 10 $mm^2$ or less, 5 $mm^2$ or less, 3 $mm^2$ or less, 1 $mm^2$ or less, 0.25 $mm^2$ or less).

Returning to FIG. 3, due to the symmetric arrangement of beams 174 and 176 with respect to prism 122, a total path length of the radiation in prism 122 is 2 g. In certain embodiments, the total path length can be 10 mm or less (e.g., 9 mm or less, 8 mm or less, 7 mm or less, 6 mm or less, 5 mm or less, 4 mm or less, 3 mm or less, 2 mm or less, 1 mm or less, 0.5 mm or less).

Prism 122 is positioned within protrusion 166 so that the exposed surface 122a of prism 122 is substantially integral with an outer surface of measurement device 100. In other words, prism 122 provides a window in the outer surface of measurement device 100 that permits incident radiation generated within the enclosure to interact with sample 190. The positioning of prism 122 relative to enclosure 156 permits contact between prism 122 and sample 190, and also ensures that the interior of enclosure 156 (e.g., the portion of enclosure 156 that includes the optical assembly) is not exposed to or contaminated by sample 190.

Referring again to FIG. 1, prism 122 is mechanically isolated from the optical assembly mounted on assembly support 152 within enclosure 156. Support base 204 and mounting plate 202, each of which contacts prism 122, are also mechanically decoupled from assembly support 152 and the optical elements mounted thereon. The mechanical isolation of prism 122 reduces coupling of mechanical perturbations into the optical assembly. For example, when prism 122 is placed in contact with sample 190, mechanical vibrations can be induced in prism 122 due to the contact. If transmitted to the optical assembly, the vibrations could, for example, displace certain optical elements from alignment. By decoupling prism 122 and the optical assembly mounted on assembly support 152, disruption of the alignment of the optical components of measurement device 100 is reduced or eliminated.

Figure 5:
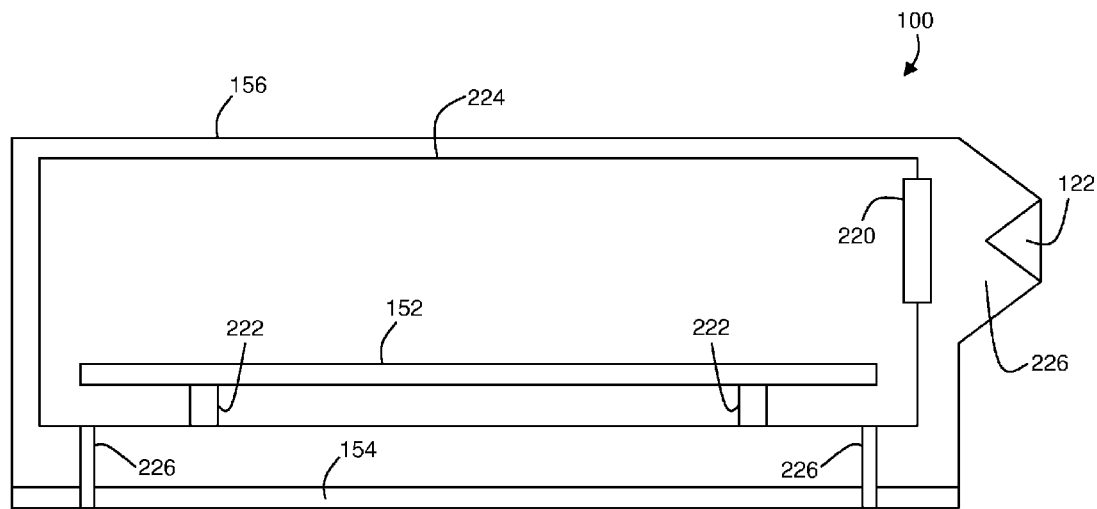
FIG. 5 is a cross-sectional view of an embodiment of a measurement device.

FIG. 5 shows a simplified side cross-sectional view of measurement device 100. Certain elements of measurement device 100 are not shown in FIG. 5 for clarity. Assembly support 152 is mounted on support legs 222, which are connected to an inner surface of hermetic enclosure 224. Hermetic enclosure 224 encloses the optical assembly mounted on support 152, and includes a window 220 that permits radiation beam 174 to leave hermetic enclosure 224, and permits radiation beam 176 to enter hermetic enclosure 224.

Hermetic enclosure 224 is hermetically sealed and mounted to enclosure 156 via posts 226. The remaining interior portion of enclosure 156, including protrusion 166, includes a liquid-proof seal but not necessarily a hermetic seal. There are a number of advantages provided by the interior architecture of measurement device 100. As discussed above, for example, prism 122 is mechanically decoupled from the optical assembly mounted to assembly support 152, which prevents transmission of large-amplitude mechanical perturbations between prism 122 and support 152 (and the components thereon).

In addition, in some embodiments, a coating 154 can be disposed on one or more inner surfaces of enclosure 156 to further reduce the amplitude of any mechanical perturbations—in particular, those that arise from handling measurement device 100—and to reduce or prevent transmission of perturbations to the elements of the optical assembly. Coating 154 can be formed from elastic materials such as silicone rubber, for example. In certain embodiments, a thickness of coating 154 is 0.3 mm or more (e.g., 0.5 mm or more, 0.7 mm or more, 1.0 mm or more, 1.5 mm or more, 2.0 mm or more, 2.5 mm or more, 3.0 mm or more, 4.0 mm or more).

During use, the potential exists for the exposed surface (e.g., surface 122a) of prism 122 to become contaminated with sample residues in such a way that surface 122a cannot be easily cleaned. In some cases, prism 122 can also become damaged (e.g., scratched) when prism 122 is used to apply pressure to samples. Contamination or damage to prism 122 may make it necessary to replace prism 122 by opening enclosure 156. However, by providing a separate hermetically sealed enclosure 224, exposure of the optical assembly mounted to assembly support 152 can be avoided, so that potential environmental contaminants and mechanical disturbances do not affect the optical components within hermetic enclosure 224. Following replacement and/or cleaning of prism 122, enclosure 156 can again be sealed with a liquid-proof seal; throughout the repair process, enclosure 224 remains hermetically sealed.

Figure 6:
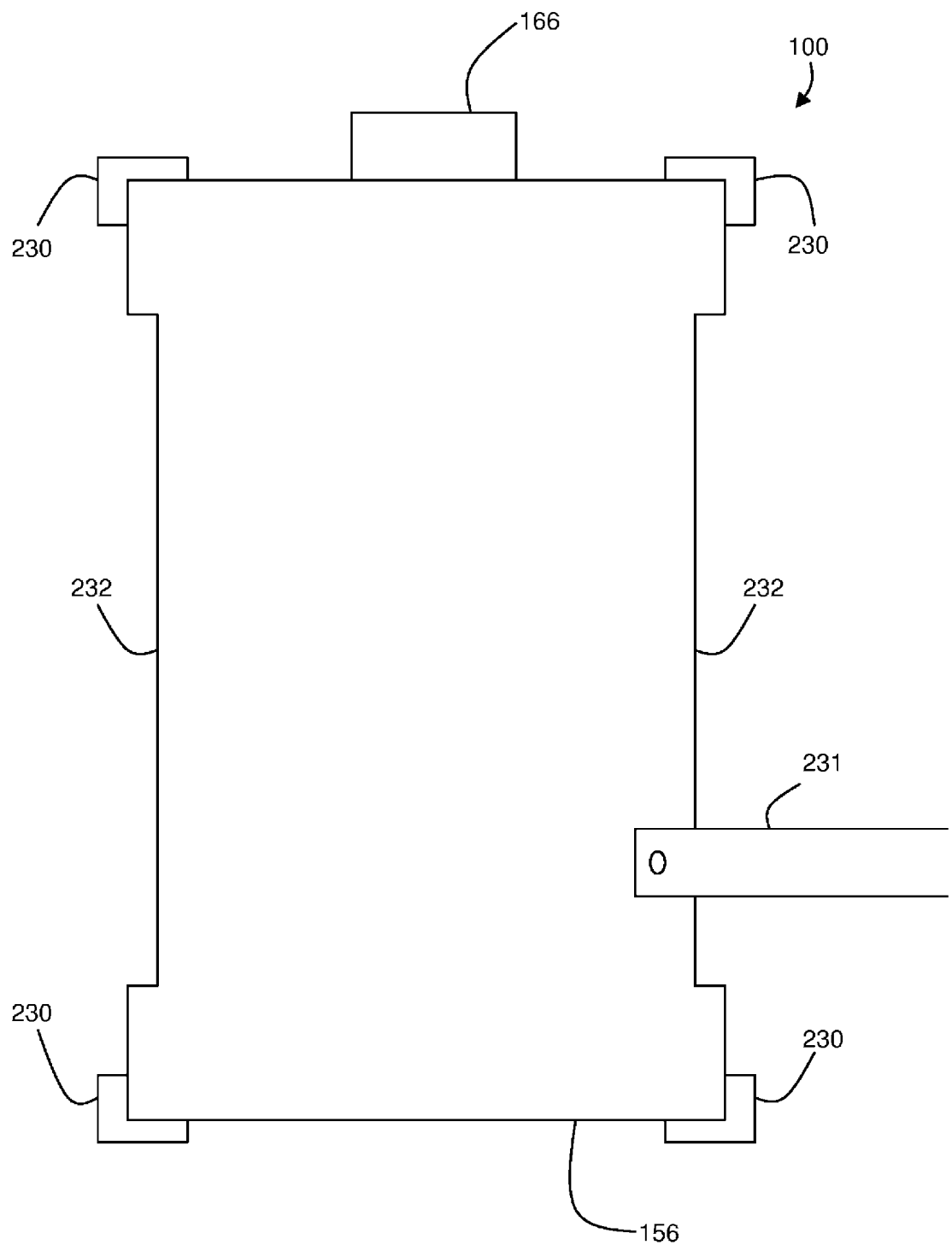
FIG. 6 is a schematic diagram of an embodiment of an enclosure.

Enclosure 156 typically has a handheld form factor, so that measurement device 100 functions as a handheld infrared spectrometer, and in particular, as a handheld Fourier transform infrared spectrometer. FIG. 6 shows a schematic diagram of enclosure 156 of measurement device 100. In some embodiments, enclosure 156 can include regions of narrowed width 232 that are positioned and dimensioned to fit the hand of a system operator, to facilitate operation of device 100 as a handheld device. In certain embodiments, enclosure 156 can also include one or more shock-absorbing external protrusions 230. The shock-absorbing external protrusions 230 can be formed from an elastic material such as rubber, for example, and are configured to reduce or eliminate the transmission of mechanical vibrations to the components within enclosure 156, and generally to protect the components of measurement device 100.

Enclosure 156 can be formed from a variety of different materials. In some embodiments, enclosure 156 is formed from a hard, lightweight, durable material such as a hard plastic material. In certain embodiments, enclosure 156 can be formed from materials such as aluminum, acrylonitrile butadiene styrene (ABS) plastic, polycarbonate, and other engineering resin plastics with relatively high impact resistance. In general, the durable material that is used to form enclosure 156 and the shock-absorbing external protrusions 230 together contribute to enclosure 156 being a rugged enclosure, configured to protect various elements positioned therein.

In some embodiments, enclosure 156 can also include a shoulder strap 231, a portion of which is shown in FIG. 6. In addition or in the alternative to shoulder straps, enclosure 156 can include a variety of other features such as protruding handles, recessed handles, clips for attaching enclosure 156 to clothing or to other supports, and other devices that enhance the portability of enclosure 156.

Referring again to FIG. 1, enclosure 156 has a maximum dimension d. In some embodiments, d is 35 cm or less (e.g., 30 cm or less, 28 cm or less, 26 cm or less, 24 cm or less, 22 cm or less, 20 cm or less, 18 cm or less). In certain embodiments, a volume of enclosure 156 is less than 750 cm$^3$ (e.g., less than 600 cm$^3$, less than 500 cm$^3$, less than 400 cm$^3$, less than 350 cm$^3$, less than 300 cm$^3$, less than 250cm$^3$, less than 200 cm$^3$, less than 175 cm$^3$, less than 150 cm$^3$). In some embodiments, a total mass of measurement device 100 can be 2 kg or less (e.g., 1.8 kg or less, 1.6 kg or less, 1.4 kg or less, 1.2 kg or less, 1.0 kg or less, 0.8 kg or less, 0.6 kg or less, 0.4 kg or less).

Figure 7:
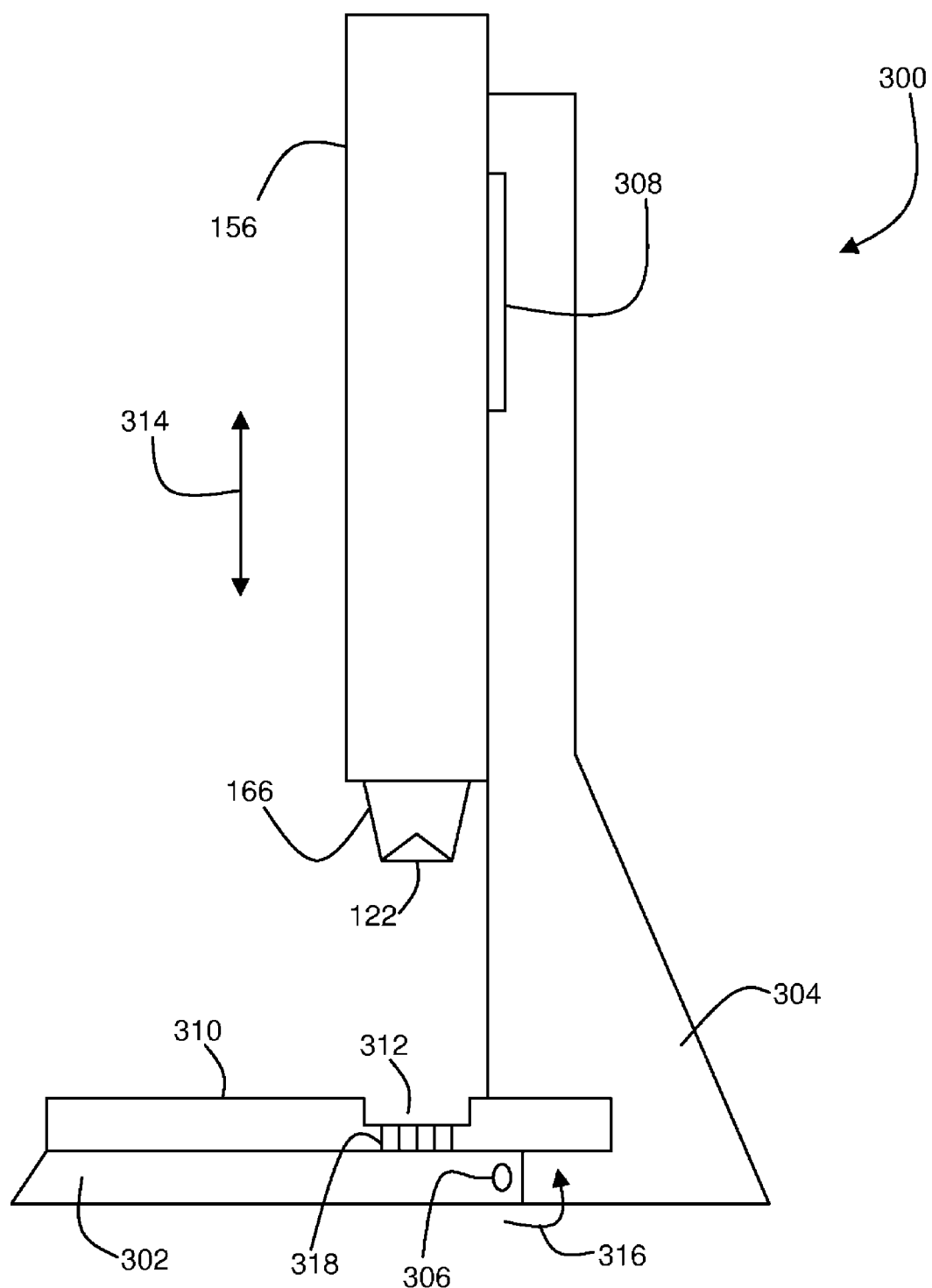
FIG. 7 is a schematic diagram of an embodiment of a portable support structure.

In some embodiments, measurement device 100 can also include a support structure that is configured to connect to enclosure 156 and to support the enclosure during sample measurements. FIG. 7 shows a schematic diagram of a support structure 300 that includes a base 302 and a mounting member 304. Support structure 300 includes an attachment mechanism 308 positioned on mounting member 304 and configured to connect to enclosure 156. Base 302 includes a stage 310, and a depressed sample region 312, configured to support a sample, is positioned in stage 310 in vertical alignment with protrusion 166. Mounting member 304 permits translation of enclosure 156 in a direction indicated by arrow 314 (e.g., substantially perpendicular to a plane that includes stage 310), so that prism 122 can be brought into contact with a sample positioned in sample region 312. In some embodiments, sample region 312 can include alignment marks 318 that guide a system operator in the placement of a sample within sample region 312 to ensure good contact between the sample and an exposed surface of prism 122.

Typically, support structure 300 is formed of a hard plastic material, for example, and structure 300 can be formed from the same material as enclosure 156. In some embodiments, support structure can be formed from a material other than plastic, such as aluminum and/or stainless steel.

In certain embodiments, support structure 300 can be a portable support structure. For example, as shown in FIG. 7, base 302 and mounting member 304 are joined at hinge 306. When not in use, support structure can be collapsed by folding mounting member 304 relative to base 302, e.g., by rotating mounting member 304 relative to base 302 in the direction indicated by arrow 316.

Support structure 300 can be used, for example, for effectively hands-free operation of measurement device 100. By connecting enclosure 156 to mounting member 304, both hands of a system operator are free to handle and position a sample 190, for example. Measurement and identification of the sample can then be initiated with a press of a single key on input device 138 by the system operator.

The preceding discussion has focused on the use of infrared absorption information to identify a sample. In some embodiments, sample information in addition to infrared absorption information can be used to identify the sample. For example, measurement device 100 can be configured to cooperate with other scanning systems to identify samples of interest. Suitable other scanning systems can include, for example, handheld and non-handheld Raman scanning systems. To identify a sample, the sample can first be scanned with a Raman scanning system that is configured to determine an identity of the sample based on Raman scattering information about the sample. The identity determined by the Raman scanning system is then transmitted to measurement device 100 and received via communication interface 142.

Measurement device 100 is also configured to separately determine an identity of the sample based on infrared absorption information. If the identities determined via infrared absorption information and Raman scattering information agree, measurement device 100 reports a successful identification to a system operator. If the identities do not agree, measurement device 100 reports a failed identification. More generally, both the Raman scanning system and measurement device 100 can be configured to determine an identity of the sample, and a numerical score or metric that is related to an extent of correspondence between the measured sample information and reference information for the sample. Measurement device 100 can then determine, based on the identities reported and the values of the metrics, whether the identification process was successful or not, and to what extent the reported identity of the sample is trustworthy.

Figure 8:
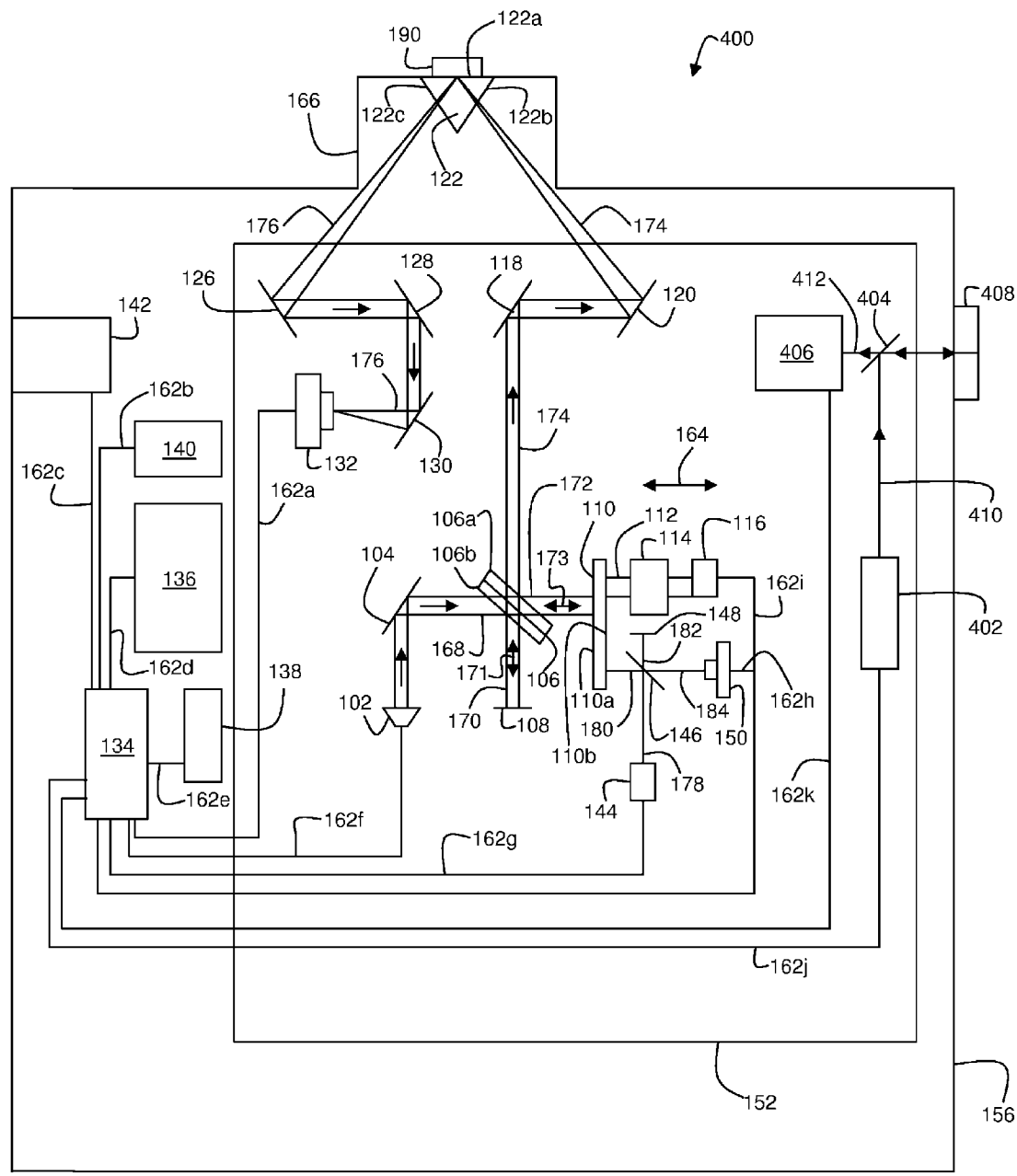
FIG. 8 is a schematic diagram of an embodiment of a measurement device that includes an infrared spectrometer and a Raman spectrometer.

In certain embodiments, an infrared absorption spectrometer and a Raman spectrometer can be combined in a single handheld instrument. FIG. 8 shows a schematic diagram of a measurement device 400 that includes an infrared scanning subsystem and a Raman scanning subsystem. The components of the infrared scanning subsystem have been discussed previously, and function in similar fashion in the embodiment shown in FIG. 1. In addition to these components, measurement device 400 also includes a radiation source 402, a beamsplitter 404, a coupling window 408, and a radiation analyzer 406. Radiation source 402 and radiation analyzer 406 are in electrical communication with processor 134 via communication lines 162j and 162k.

As shown in FIG. 8, protrusion 166—which includes prism 122—forms a first aperture, and the infrared scanning subsystem is configured to direct incident radiation to a sample when the sample is in contact with prism 122 to determine infrared absorption information about the sample.

Coupling window 408 forms a second aperture. The Raman scanning subsystem is configured to direct incident radiation to the sample when the sample is positioned in proximity to coupling window 408 to determine Raman scattering information about the sample. Radiation source 402, after receiving a suitable control signal from processor 134, generates incident radiation 410. A portion of incident radiation 410 reflects from dichroic beamsplitter 404 and leaves enclosure 156 through coupling window 408. Radiation 410 is incident on the sample, and a portion of the radiation is scattered by the sample as scattered radiation 412. The scattered radiation (or a portion thereof) passes through dichroic beamsplitter 404 and enters radiation analyzer 406. Once inside radiation analyzer 406, reflected radiation 412 is manipulated (e.g., by dispersing scattered radiation 412 into a plurality of wavelength components) and measured (e.g., using one or more photoelectric or CCD detectors) to derive Raman scattering information about the sample. Radiation analyzer 406 can include one or more dispersive elements such as gratings and/or prisms, various lenses and/or mirrors for collimating, focusing, and re-directing radiation, or more filter elements for reducing radiation intensity, and one or more beamsplitting elements for dividing radiation beams into multiple beams. Radiation analyzer 406 can also include various types of radiation detectors, and a processor.

The measured Raman scattering information is then transmitted to processor 134. Suitable methods for measuring Raman scattering information, and suitable systems and components thereof, are described, for example, in U.S. patent application Ser. No. 11/837,284 entitled "OBJECT SCANNING AND AUTHENTICATION" by Kevin J. Knopp et al., filed on Aug. 10, 2007, the entire contents of which are incorporated by reference herein.

Typically, to perform a measurement on a sample, the sample is first positioned in proximity to coupling window 408 and Raman scattering information about the sample is measured. Then, measurement device 400 is re-oriented (or the sample is moved) so that the sample contacts the exposed surface of prism 122, and infrared absorption information about the sample is measured. The Raman scattering and infrared absorption information is transmitted to processor 134, and the processor identifies the sample based on the two types of information.

Processor 134 can determine an identity of the sample using a variety of different algorithms that process the Raman scattering information and infrared absorption information about the sample. In some embodiments, for example, processor 134 can be configured to compare the Raman scattering information about the sample to a database of reference Raman scattering information stored in storage unit 140 for a variety of samples, to determine whether the sample Raman scattering information matches reference Raman scattering information for a particular substance. If a match is found, a numerical score or metric can be calculated which reflects an extent of correspondence between the sample and reference Raman scattering information. As discussed previously, the stored reference Raman scattering information can be updated periodically via communication interface 142.

Similarly, processor 134 can compare the sample infrared absorption information to reference infrared absorption information stored in storage unit 140 to determine whether the sample infrared absorption information matches reference information for a particular substance. If a match is found, a numerical score or metric can be calculated which reflects an extent of correspondence between the sample and reference infrared absorption information.

Processor 134 then compares the substances matched by the sample Raman scattering information and infrared absorption information. If the matched substances are the same for each, processor 134 outputs a signal to display 136 that indicates to a system operator a successful identification of the sample. The signal can include the identity of the sample, and one or more metrics that are calculated from the comparisons of the sample and reference Raman scattering information and/or infrared absorption information. The one or more metrics can provide an indication of the extent of correspondence between sample and reference Raman scattering information and/or sample and reference infrared absorption information, for example. Algorithms and suitable metrics for comparing sample and reference Raman scattering information and/or sample and reference infrared absorption information are generally disclosed, for example, in U.S. Pat. No. 7,254,501 entitled "SPECTRUM SEARCHING METHOD THAT USES NON-CHEMICAL QUALITIES OF THE MEASUREMENT", issued on Aug. 7, 2007, the entire contents of which are incorporated by reference herein.

Returning to FIG. 1, in some embodiments, measurement device 100 can include only an infrared scanning subsystem (e.g., no Raman scanning system), and processor 134 can be configured to receive sample Raman scattering information measured by another device. For example, a Raman scanning device can be configured to scan samples and transmit Raman scattering information obtained from the samples over a wired or wireless network to measurement device 100. Measurement device 100 can be configured to receive the sample Raman scattering information via communication interface 142, and to compare the sample Raman scattering information to reference Raman scattering information stored in storage unit 140 to determine an identity of the sample. Measurement device 100 can also be configured to measure sample infrared absorption information as discussed above, and to compare the infrared absorption information about the sample to reference infrared absorption information to determine an identity of the sample. Results from the comparisons of the sample and reference Raman scattering information and infrared absorption information can then be combined in the manner disclosed above.

In certain embodiments, processor 134 can be configured to automatically determine (or accept similar directions from a system operator) whether to use only Raman scattering information about the sample to determine the sample's identity, whether to use only infrared absorption information about the sample to determine the sample's identity, or whether to use a combination of both Raman scattering information and infrared absorption information. Typically, for example, processor 134 can be configured to assign relative weights ranging from 0 to 1 to the sample Raman scattering information and infrared absorption information. The assignment of a weight of 0 corresponds to non-use of the information.

Figure 9A:
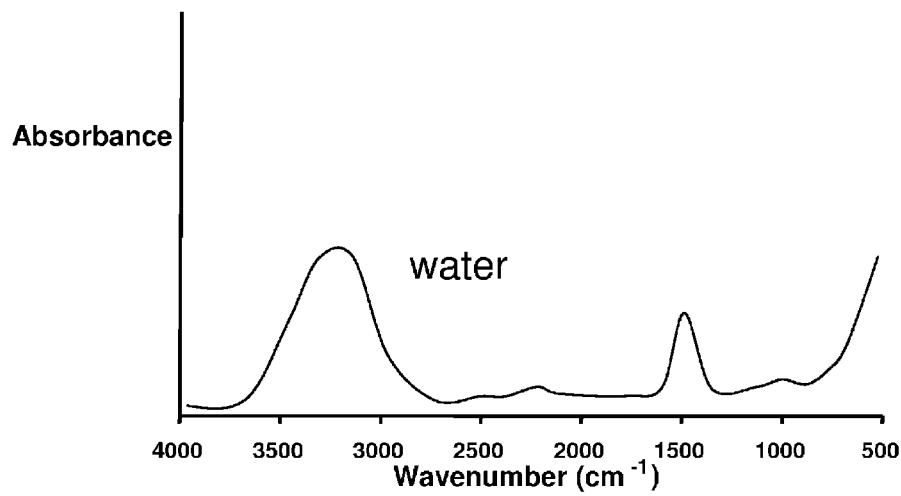
FIGS. 9A and 9B are plots of infrared absorption information and Raman scattering information for a sample of 3% hydrogen peroxide in water.
Figure 9B:
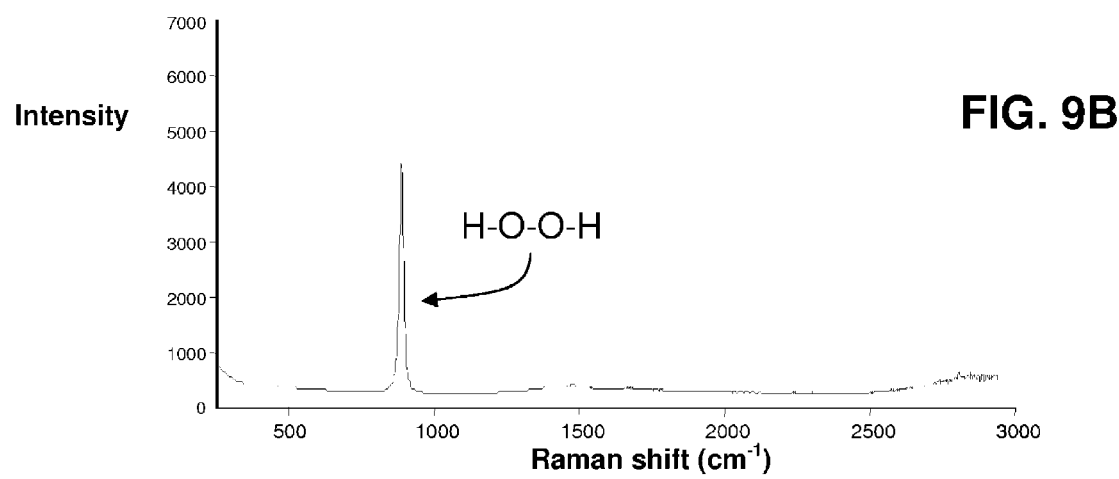

Certain types of samples, for example, are aqueous-based, or include large numbers of alcohols and/or hydroxyl (—OH) groups. In infrared absorption spectra, —OH groups typically exhibit a strong, broad, featureless stretching band at about 3300 cm$^{-1}$. This broad band can obscure other spectral features which could otherwise be used to identify the sample. Therefore, in some embodiments, processor 134 can be configured to reduce reliance on infrared absorption information when identifying the sample, and to use primarily Raman scattering information to identify the sample, since Raman scattering spectra typically do not include such broad —OH bands (and are not sensitive to water). FIGS. 9A and 9B show examples of infrared absorption and Raman scattering information, respectively, measured for a sample that includes a 3% hydrogen peroxide solution in water. The infrared absorption spectrum includes a broad, featureless —OH band that corresponds to both water and hydrogen peroxide. The Raman scattering spectrum includes a narrow band that corresponds approximately only to hydrogen peroxide. In general, the use of infrared absorption information can be reduced relative to Raman scattering information by processor 134 to circumvent a number of troublesome infrared spectral features, including —OH stretching bands as disclosed above.

Figure 10A:
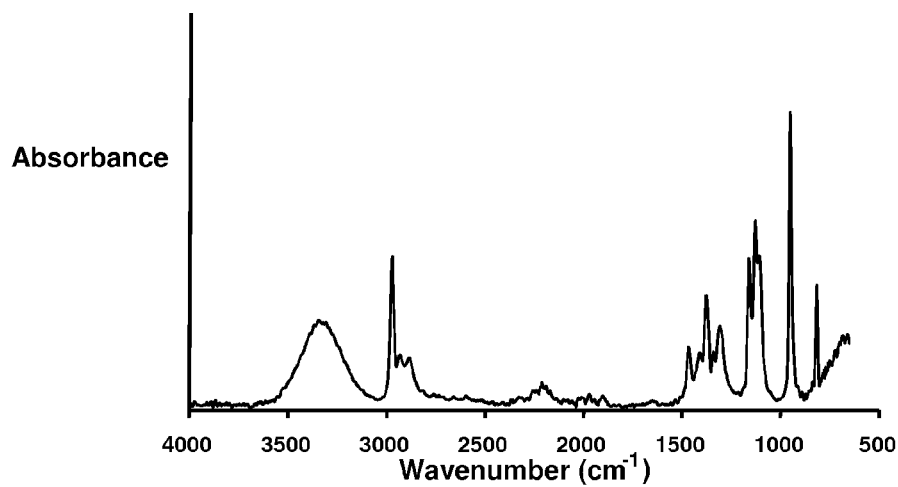
FIGS. 10A and 10B are plots of infrared absorption information and Raman scattering information for a sample of isopropanol.
Figure 10B:
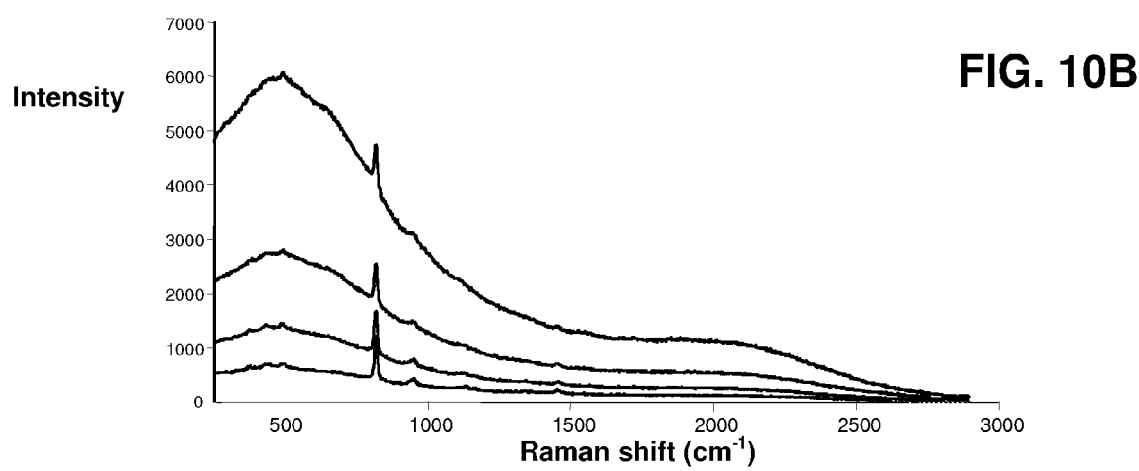

Certain types of samples exhibit large background fluorescence, which reduces the accuracy of measured Raman scattering information. Typically, for example, the large background fluorescence appears in Raman spectra as a broad, featureless band that can obscure underlying peaks, making identification of the sample on the basis of the Raman scattering information difficult. Processor 134 can be configured to reduce reliance on Raman scattering information when identifying the sample, and to use primarily infrared absorption information to identify the sample, since infrared absorption spectra are not typically perturbed by background fluorescence. FIGS. 10A and 10B show examples of infrared absorption and Raman scattering information, respectively, measured for a sample of isopropanol. The Raman spectrum of isopropanol includes a featureless, broad fluorescence band that nearly obscures the underlying bands. The infrared absorption spectrum includes a relatively small —OH stretching band that does not overwhelm the spectrum, and several well-resolved bands at energies lower than 3000 cm$^{-1}$ that can be used to identify the sample. In general, the use of Raman scattering information can be reduced relative to infrared absorption information by processor 134 to circumvent a number of troublesome Raman spectral features, including fluorescence bands as disclosed above.

Figure 11A:
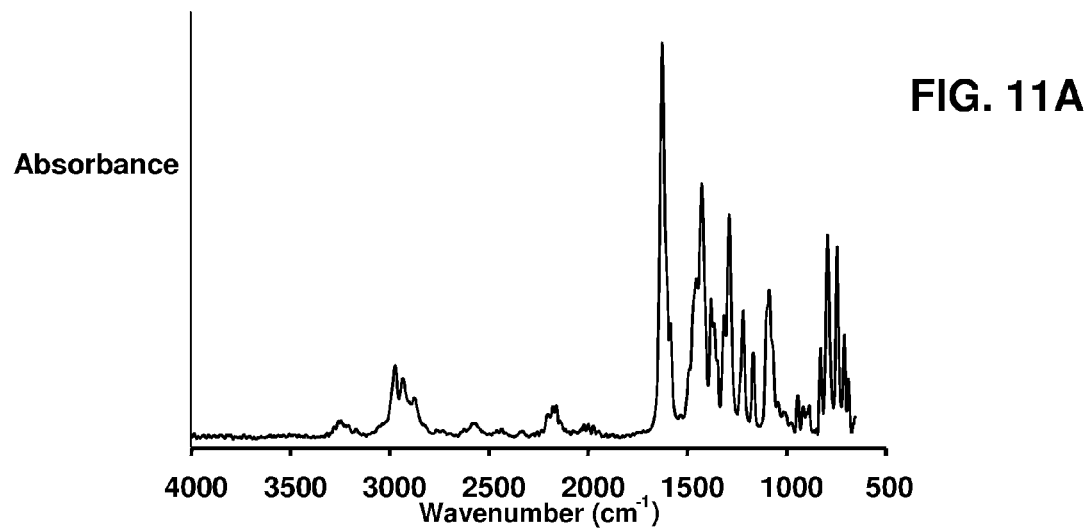
FIGS. 11A and 11B are plots of infrared absorption information and Raman scattering information for a sample of a pesticide.
Figure 11B:
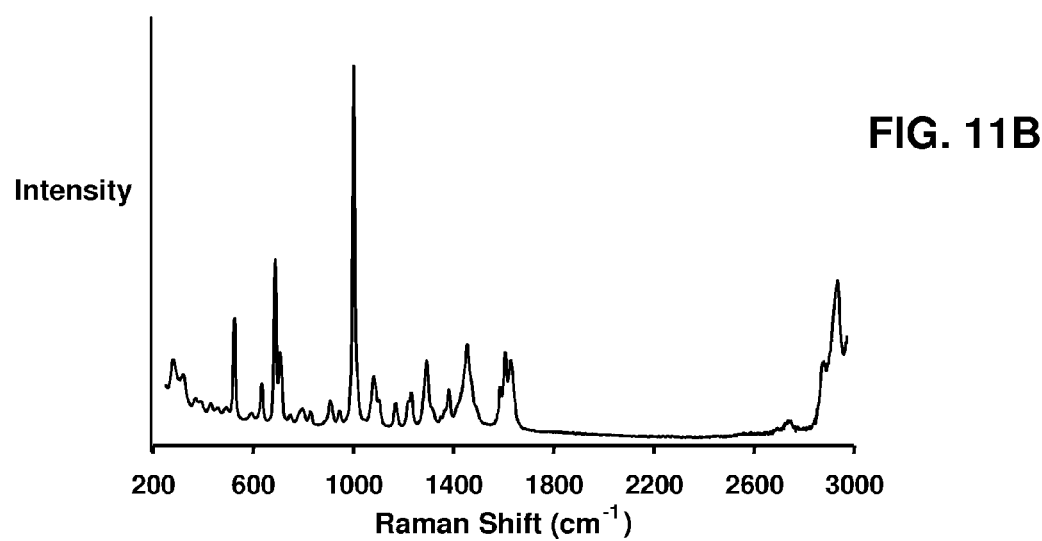

In some embodiments, both Raman scattering information and infrared absorption information can be used to identify a sample in complementary fashion. FIGS. 11A and 11B show examples of infrared absorption and Raman scattering information, respectively, measured for a sample of DEET pesticide. Each of the Raman scattering and infrared absorption spectra includes multiple well-resolved bands, so that both the Raman scattering and infrared absorption information can be used by processor 134 to determine an identity of the sample.

Referring again to FIG. 8, radiation source 402 can include one or more of a variety of sources including, for example, laser diode sources, light-emitting diode sources, and laser sources. Incident radiation 410 provided by source 402 generally includes a distribution of radiation wavelengths. In some embodiments, a center wavelength of the distribution is 800 nm or less (e.g., 700 nm or less, 600 nm or less, 500 nm or less, 450 nm or less, 400 nm or less, 350 nm or less, 300 nm or less, 250 nm or less). In particular, because Raman scattering cross-sections for various samples generally increase with decreasing wavelength, greater Raman scattering signal strength can be obtained by generating incident radiation 410 with a center wavelength less than 450 nm.

The intensity of incident radiation 410 can generally be selected as desired to generate a Raman scattering signal from the sample. Typically, the intensity of incident radiation 410 can be tens or hundreds of milliwatts, for example. However, in certain embodiments (such as, for example, embodiments where a center wavelength of incident radiation 410 is less than 450 nm), an intensity of incident radiation 410 can be 20 mW or less (e.g., 10 mW or less, 5 mW or less, 4 mW or less, 3 mW or less, 2 mW or less, 1 mW or less, 0.5 mW or less). In some embodiments, relatively low intensities can be used to prevent possible detonation of unknown substances due to heating of the substances by radiation 410.

Figure 12:
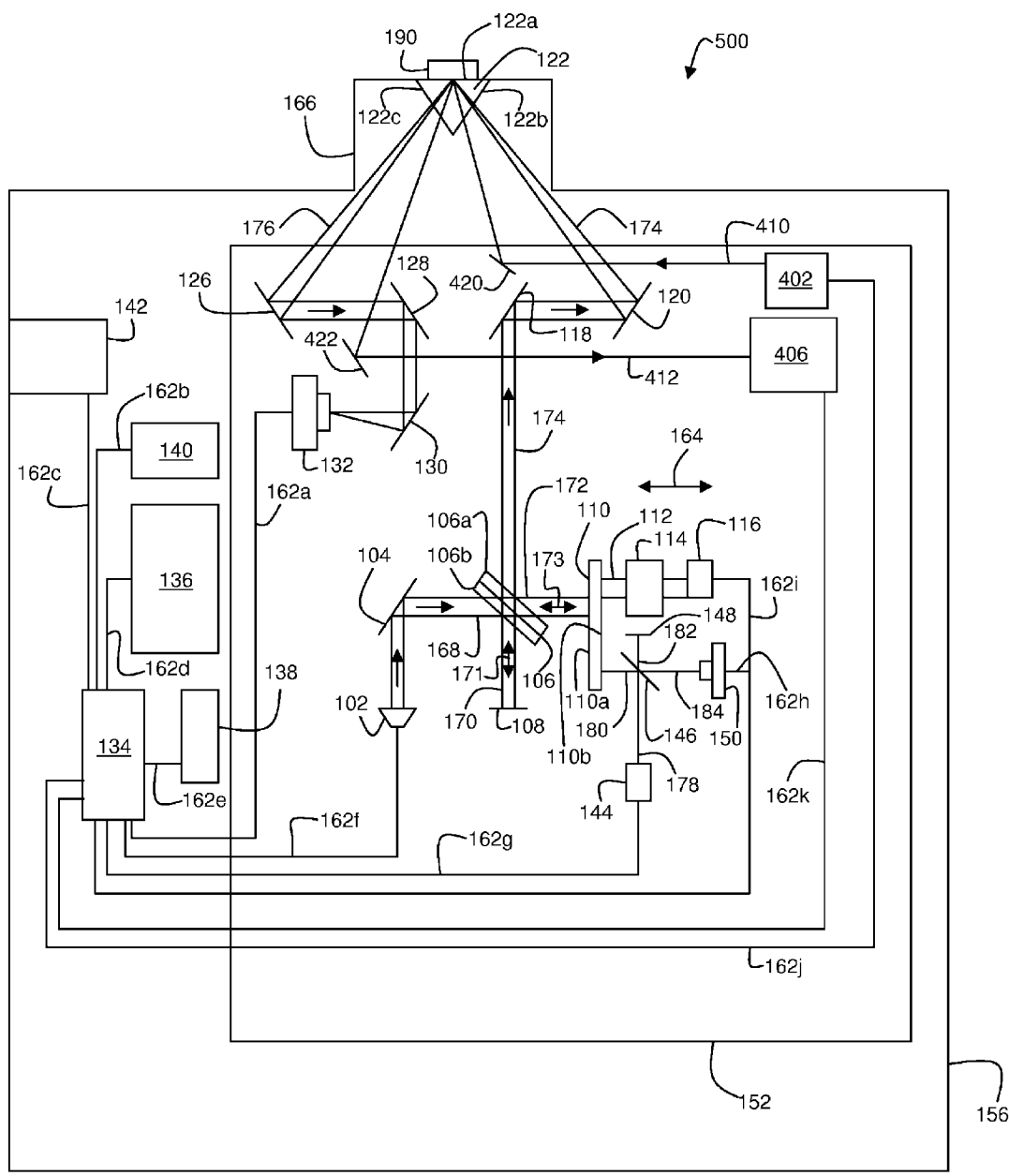
FIG. 12 is a schematic diagram of another embodiment of a measurement device that includes an infrared spectrometer and a Raman spectrometer.

In some embodiments, measurement devices can include both infrared and Raman scanning subsystems, and both the infrared and Raman subsystems can be configured to direct incident light to a sample via prism 122. The subsystems can be configured so that the incident light from each subsystem interrogates a common region of the sample, which reduces measured signal noise due to spatial inhomogeneity of the sample. FIG. 12 shows a measurement device 500 where incident radiation from each of the infrared and Raman scanning subsystems passes into prism 122 and is incident on sample 190. Many of the components in FIG. 12 have been previously discussed. Source 402 generates incident radiation beam 410 that is directed by mirror 420 to enter prism 122 and interact with the sample via surface 122*a*. Scattered radiation beam 412 is directed by mirror 422 to enter radiation analyzer 406. Radiation analyzer 406 disperses wavelength components of scattered radiation beam 412 and measures the dispersed components to determine Raman scattering information about the sample.

In the embodiment shown in FIG. 12, both the infrared scanning subsystem and the Raman scanning subsystem direct incident light to a common location on sample 190. In addition to reducing noise due to spatial inhomogeneity in the measured sample information, the configuration of measurement device 500 shown in FIG. 12 is simpler than the configuration of measurement device 400 in FIG. 8, requiring fewer apertures. Further, measurements of both Raman scattering information and infrared absorption from the sample can be made without re-positioning measurement device 500 relative to sample 190.

The measurement devices disclosed herein can be used for a variety of sample identification applications. For example, the measurement devices disclosed herein can be used in airports and other transportation hubs, in government buildings, and in other public places to identify unknown (and possibly suspicious) substances, and to detect hazardous and/or prohibited substances. Airports, in particular, restrict a variety of substances from being carried aboard airplanes. The measurement devices disclosed herein can be used to identify substances that are discovered through routine screening of luggage, for example. Identified substances can be compared against a list of prohibited substances (e.g., a list maintained by a security authority such as the Transportation Safety Administration) to determine whether confiscation and/or further scrutiny by security officers is warranted.

Law enforcement officers can also use the portable measurement devices disclosed herein to identify unknown substances, including illegal substances such as narcotics. Accurate identifications can be performed in the field by on-duty officers.

The measurement systems disclosed herein can also be used to identify a variety of industrial and pharmaceutical substances. Shipments of chemicals and other industrial materials can be quickly identified and/or confirmed on piers and loading docks, prior to further transport and/or use of the materials. Further, unknown materials can be identified to determine whether special handling precautions are necessary (for example, if the materials are identified as being hazardous). Pharmaceutical compounds and their precursors can be identified and/or confirmed prior to production use and/or sale on the market.

Generally, a wide variety of different samples can be identified using the measurement devices disclosed herein, including pharmaceutical compounds (and precursors thereof), narcotics, industrial compounds, explosives, energetic materials (e.g., TNT, RDX, HDX, and derivatives of these compounds), chemical weapons (and portions thereof), household products, plastics, powders, solvents (e.g., alcohols, acetone), nerve agents (e.g., soman), oils, fuels, pesticides, peroxides, beverages, toiletry items, other substances (e.g., flammables) that may pose a safety threat in public and/or secure locations, and other prohibited and/or controlled substances.

Other embodiments are in the claims.

What is claimed is:

1. An apparatus, comprising:
a handheld enclosure including an aperture;
a prism mounted in the enclosure so that a surface of the prism is exposed through the aperture;
an optical assembly contained within the enclosure, the optical assembly comprising a radiation source and a radiation detector, the source being configured to direct radiation towards the prism and the detector being configured to detect radiation from the source reflected from the exposed surface of the prism;
an electronic processor contained within the enclosure, the electronic processor being in communication with the detector;
wherein the radiation source and the radiation detector are mechanically isolated from the prism;
and wherein the apparatus is configured so that, during operation, the electronic processor determines information about a sample placed in contact with the exposed surface of the prism based on radiation reflected from the exposed prism surface while it is in contact with the sample.

2. An apparatus according to claim 1 wherein the radiation source and the radiation detector are positioned on a first supporting member, the prism is positioned on a second supporting member, and the first and second supporting members do not contact each other.

3. An apparatus according to claim 2, wherein the first supporting member, the radiation source, and the radiation detector are positioned within a housing, and wherein the housing is positioned within the enclosure.

4. An apparatus according to claim 1 wherein the optical assembly comprises radiation sources, mirrors, beamsplitters, and detectors which are mounted on a support which is mechanically isolated from the prism.

5. An apparatus according to claim 3, wherein the housing is hermetically sealed.

6. An apparatus according to claim 4 wherein the optical assembly is connected to an inner surface of a hermetic enclosure.

7. An apparatus according to claim 4 wherein the hermetic enclosure includes a window that permits a radiation beam to leave the hermetic enclosure and permits a radiation beam to enter the hermetic enclosure.

8. An apparatus according to claim 3, further comprising a coating disposed on at least some inner surfaces of the enclosure.

9. An apparatus according to claim 8, wherein the coating comprises a silicone rubber material.

10. An apparatus according to claim 9, wherein a thickness of the coating is 0.5 mm or more.

11. An apparatus according to claim 1 wherein the aperture includes a protrusion extending outward from the enclosure and wherein the prism is positioned within the aperture.

12. An apparatus according to claim 11 wherein the protrusion extends outward from the enclosure a distance of 10 mm or more.

13. An apparatus, comprising:
a handheld enclosure including an aperture;

a prism mounted in the enclosure so that a surface of the prism is exposed through the aperture;

an optical assembly contained within the enclosure, the optical assembly comprising a radiation source and a radiation detector, the source being configured to direct radiation towards the prism and the detector being configured to detect radiation from the source reflected from the exposed surface of the prism;

an electronic processor contained within the enclosure, the electronic processor being in communication with the detector, wherein the apparatus is configured so that, during operation, the electronic processor determines information about a sample placed in contact with the exposed surface of the prism based on radiation reflected from the exposed prism surface while it is in contact with the sample;

and wherein the aperture includes a protrusion extending outward from the enclosure and wherein the prism is positioned within the aperture.

14. An apparatus according to claim 13 wherein the protrusion extends outward from the enclosure a distance of 10 mm or more.

15. An apparatus according to claim 13 wherein an exposed surface of the prism is substantially integral with an outer surface of the apparatus.

* * * * *